United States Patent
Kudo et al.

(10) Patent No.: US 9,169,324 B2
(45) Date of Patent: Oct. 27, 2015

(54) REDUCER OF IMMUNOSUPPRESSION BY TUMOR CELL AND ANTITUMOR AGENT USING THE SAME

(71) Applicant: Keio University, Minato-ku, Tokyo (JP)

(72) Inventors: Chie Kudo, Tokyo (JP); Yutaka Kawakami, Tokyo (JP)

(73) Assignee: Keio University, Tokyo (JP)

( * ) Notice: Subject to any disclaimer, the term of this patent is extended or adjusted under 35 U.S.C. 154(b) by 597 days.

(21) Appl. No.: 13/627,655

(22) Filed: Sep. 26, 2012

(65) Prior Publication Data

US 2013/0115225 A1 May 9, 2013

Related U.S. Application Data

(63) Continuation of application No. 12/674,881, filed as application No. PCT/JP2008/064987 on Aug. 22, 2008, now abandoned.

(30) Foreign Application Priority Data

Aug. 24, 2007 (JP) ................ 2007-218977

(51) Int. Cl.

| A61K 39/395 | (2006.01) |
|---|---|
| C07K 16/28 | (2006.01) |
| A61K 31/00 | (2006.01) |
| A61K 38/17 | (2006.01) |
| A61K 38/19 | (2006.01) |
| C07K 14/47 | (2006.01) |
| C07K 16/18 | (2006.01) |
| C07K 16/24 | (2006.01) |
| C07K 16/30 | (2006.01) |
| C12N 5/09 | (2010.01) |
| C12N 15/113 | (2010.01) |
| A61K 39/00 | (2006.01) |

(52) U.S. Cl.
CPC ............ *C07K 16/2866* (2013.01); *A61K 31/00* (2013.01); *A61K 38/1709* (2013.01); *A61K 38/1793* (2013.01); *A61K 38/195* (2013.01); *C07K 14/4702* (2013.01); *C07K 16/18* (2013.01); *C07K 16/24* (2013.01); *C07K 16/30* (2013.01); *C12N 5/0693* (2013.01); *C12N 15/113* (2013.01); *A61K 2039/505* (2013.01); *C07K 2317/73* (2013.01); *C12N 2310/14* (2013.01); *C12N 2501/148* (2013.01); *C12N 2502/1114* (2013.01); *C12N 2502/1157* (2013.01); *C12N 2502/30* (2013.01); *C12N 2510/00* (2013.01)

(58) Field of Classification Search
None
See application file for complete search history.

(56) References Cited

FOREIGN PATENT DOCUMENTS

| EP | 0478101 A2 | 4/1992 |
|---|---|---|
| JP | 2005-526842 | 9/2005 |
| JP | 2005-536534 | 12/2005 |
| JP | 2006-206538 | 8/2006 |
| WO | WO 2005/062972 | 7/2005 |
| WO | WO 2006/109301 | 10/2006 |

OTHER PUBLICATIONS

Johnston et al., Oncogene. Nov. 9, 2000;19(47):5348-58.*
Trojan et al., Anticancer Res. Jan.-Feb. 2005;25(1A):183-91.*
Rosivatz et al., Virchows Arch. Mar. 2006;448(3):277-87.*
Hardy et al., Am J Pathol. Sep. 2007;171(3):1037-46.*
Kudo-Saito et al., "Targeting FSTL1 prevents tumor bone metastasis and consequent immune dysfunction," Cancer Res. 73:6185-6193 (2013).
Kudo-Saito, "FSTL1 promotes bone metastasis by causing immune dysfunction," OncoImmunology 2:e26528-1-e26528-2 (2013).
Abstract of Avolio et al. "RNA Interference Targeting the R2 Subunit of Ribonucleotide Reductase Inhibits Growth of Tumor Cells in vitro and in vivo" *Anticancer Drugs* 18(4): 377-388 (2007).
Atabani et al., "Association of CTLA4 Polymorphism with Regulatory T Cell Frequency," *Eur. J. Immunol.* 35(7): 2157-2162 (2005).
Bisikirska et al., "TCR Stimulation with Modified Anti-CD3 mAb Expands CD8+ T Cell Population and Induces CD8+CD25+ Tregs," *J. Clin. Invest.* 115(10): 2904-2913 (2005).
Castle et al., "Antisense-Mediated Reduction in Thrombospondin Reverses the Malignant Phenotype of a Human Squamous Carcinoma," *J. Clin. Invest.* 87(6):1883-1888 (1991).
Comer et al. "Effect of Administration of CTLA4-Ig as Protein or cDNA on Corneal Allograft Survival" *Invest. Ophthalmol. Vis. Sci.* 43(4): 1095-1103 (2002).
Cytokine Zoshoku Inshi Yogo Library, Yodosha Co., Ltd., Mar. 1, 2005, p. 147.
Depaolo et al., "CC Chemokine Ligand 2 and Its Receptor Regulate Mucosal Production of IL-12 and TGF-β In High Dose Oral Tolerance," *J. Immunol.* 171(7):3560-3567 (2003).
El Andaloussi and Lesniak, "An Increase in CD4+CD25+FOXP3+ Regulatory T Cells in Tumor-Infiltrating Lymphocytes of Human Glioblastoma Multiforme," *Neuro. Oncol.* 8(3): 234-243 (2006).
Fang et al. "Stable Antibody Expression at Therapeutic Levels Using the 2A Peptide" *Nature Biotechnology* 23(5): 584-590 (2005).
Fichtner-Feigl et al., "IL-13 Signaling Through the IL-13$\alpha_2$ Receptor Is Involved in Induction of TGF-$\beta_1$ Production and Fibrosis," *Nat. Med.* 12(1):99-106 (2006).
Fontenot et al., "Foxp3 Programs the Development and Function of CD4+CD25+ Regulatory T Cells," *Nat. Immunol.* 4(4): 330-336 (2003).

(Continued)

*Primary Examiner* — Zachary Skelding
(74) *Attorney, Agent, or Firm* — Clark & Elbing LLP

(57) ABSTRACT

The invention features methods for inhibiting enhancement of expression of a FoxP3 gene in a cell, methods for inhibiting induction of differentiation of a cell into a regulatory T cell, methods for reducing immunosuppression, methods for stimulating tumor immunity, and methods for treating a patient with a tumor. The methods of the invention involve suppressing function of an FSTL1 protein in the cell. In the methods of the invention, function of an FSTL1 protein in the cell may be suppressed using an anti-FSTL1 antibody.

1 Claim, 24 Drawing Sheets

(56) References Cited

OTHER PUBLICATIONS

Fontenot et al., "Regulatory T Cell Lineage Specification by the Forkhead Transcription Factor Foxp3," *Immunity* 22(3): 329-341 (2005).
Hickey, "Leukocyte Traffic in the Central Nervous System: The Participants and Their Roles," *Semin. Immunol.* 11(2): 125-137 (1999).
Hori et al., "Control of Regulatory T Cell Development by the Transcription Factor Foxp3," *Science* 299(5609): 1057-1061 (2003).
Ichihara et al., "Increased Populations of Regulatory T Cells in Peripheral Blood and Tumor-Infiltrating Lymphocytes in Patients with Gastric and Esophageal Cancers," *Clin. Cancer Res.* 9(12): 4404-4408 (2003).
Igarashi and Kato, "Tensha Inshi Snail no Vitamin D Juyotai o Kaishita Hito Daichogan eno Sayo no Kaimei," *Vitamins* 79(12):595-596 (2005).
English translation of Igarashi and Kato, "Elucidation of the Activity of Transcription Factor SNAIL on Human Colon Cancer via Vitamin D Receptor," Vitamin (*The Vitamin Society of Japan, Kyoto*) 79(12):595-596 (2005).
Kayao et al. "Hakkekyu Saibo no Shozoki eno Shinjun to sono Saibozo," *J. Jpn. Soc. Clin. Cytol.* 44(2 supplementary issue):340 E5 (2005).
English translation of Kayao et al., "Invasion of Leukemia Cells into Various Organs and their Cellular Morphology," *The Journal of the Japanese Society of Clinical Cytology* 44(Suppl. 2):340 (2005).
Jiang et al. "Gene Therapy Using Adenovirus-Mediated Full-length Anti-HER-2 Antibody for HER-2 Overexpression Cancers" *Clin. Cancer Res.* 12:6179-6185 (2006).
Jiang and Chess, "An Integrated View of Suppressor T Cell Subsets in Immunoregulation," *J. Clin. Invest.* 114(9): 1198-1208 (2004).
Johnson et al., "Relationships Between Drug Activity and NCI Preclinical In Vitro and In Vivo Models and Early Clinical Trials," *Br. J. Cancer* 84:1424-1431 (2001).
Joshi et al. "P276-00, a Novel Cyclin-Dependent Inhibitor Induces $G_1$-$G_2$ Arrest, Shows Antitumor Activity on Cisplatin-Resistant Cells and Significant in vivo Efficacy in Tumor Models" *Mol. Cancer Ther.* 6(3):926-934 (2007).
Liyanage et al., "Prevalence of Regulatory T Cells Is Increased in Peripheral Blood and Tumor Microenvironment of Patients with Pancreas or Breast Adenocarcinoma," *J. Immunol.* 169(5): 2756-2761 (2002).
Miyara and Sakaguchi, "Natural Regulatory T Cells: Mechanisms of Suppression," *Trends. Mol. Med.* 13(3):108-116 (2007).
Miyoshi et al., "Tensha Inshi Snail, SIP1 wa Kangan Saibo no E-cadherin Idenshi Hatsugen o Yokusei suru to Tomoni Shinjunno o Koshin Saseru," *J. Jpn. Surg. Soc.* 104:556-557 PS4053-6 (2003).
English translation of Miyoshi et al., "Transcription Factors Snail and SIP1 Suppress Expression of E-cadherin Gene as well as Enhance Invasiveness in Hepatic Cancer Cell," *Journal of Japan Surgical Society* 104(extra edition):556-557 (2003).
Murakami et al., "Seigyosei T-Saibo no Yudo to sono Oyo," *Transplantation Now* 20(4):335-340 (2007).
English translation of Murakami et al., "Manipulation of Regulatory T Cells and Their Potential Applications," *Transplantation Now (Kyou no ishoku)* 20(4):335-340, 2007, published Aug. 3, 2007.
Nishikawa and Shiku, "Seigyosei T-Saibo ni yoru Men'eki Yokusei to sono Kofufuku-Yuko na Gan Vaccine Ryoho no Kaihatsu ni Mukete," *Igaku no Ayumi* 221(8):631-636 (2007).
English translation of Nishikawa and Shiku, "Suppression of Immune Response with Regulatory T Cells and Strategy to Overcome the Suppressive Activity," *Journal of Clinical and Experimental Medicine (Igaku no ayumi)* 221(8):631-636 (2007).
Patil et al., "DNA-Based Therapeutics and DNA Delivery Systems: A Comprehensive Review," *The AAPS Journal* 7:Article 9, E61-E77 (2005).
Peinado et al., "Snail, Zeb and bHLH Factors in Tumour Progression: An Alliance Against the Epithelial Phenotype?," *Nat. Rev. Cancer* 7(6): 415-428 (2007).

Pérez-Mancera et al., "Cancer Development Induced by Graded Expression of Snail in Mice," *Hum. Mol. Genet.* 14:3449-3461 (2005).
Sakaguchi et al., "Immunologic Tolerance Maintained by CD25+ CD4+ Regulatory T Cells: Their Common Role in Controlling Autoimmunity, Tumor Immunity, and Transplantation Tolerance," *Immunol. Rev.* 182: 18-32 (2001).
Sasada et al., "CD4+CD25+ Regulatory T Cells in Patients with Gastrointestinal Malignancies: Possible Involvement of Regulatory T Cells in Disease Progression," *Cancer* 98(5): 1089-1099 (2003).
Seo et al., "Interleukin-10 Expressed at Early Tumour Sites Induces Subsequent Generation of CD4+ T-Regulatory Cells and Systemic Collapse of Antitumour Immunity," *Immunol.* 103(4):449-457 (2001).
Skapenko et al., "The IL-4 Receptor α-Chain-Binding Cytokines, IL-4 and IL-13, Induce Forkhead Box P3-Expressing CD25+CD4+ Regulatory T Cells from CD25−CD4+ Precursors," *J. Immunol.* 175(9):6107-6116 (2005).
Stover et al. "The Small Molecule Tyrosine Kinase Inhibitor AMN107 Inhibits TEL-PDGFR β and FIP1L1-PDGFRα in vitro and in vivo" *Blood* 106(9):3206-3213 (2005).
*The Merck Manual of Diagnosis and Therapy*, 18th Edition, Japanese version. Porter, Robert S. (Ed). Index of Section 11, "Hematology and Oncology," pp. 1083-1086.
English Translation of *The Merck Manual of Diagnosis and Therapy*, 18th Edition, Japanese version. Porter, Robert S. (Ed). Index of Section 11, "Hematology and Oncology," chapter headings 142-144.
Turk et al., "Multiple Pathways to Tumor Immunity and Concomitant Autoimmunity," *Immunol. Rev.* 188: 122-135 (2002).
Voskoglou-Nomikos et al., "Clinical Predictive Value of the In Vitro Cell Line, Human Xenograft, and Mouse Allograft Preclinical Cancer Models," *Clin. Cancer Research* 9:4227-4239 (2003).
Wolf et al., "Increase of Regulatory T Cells in the Peripheral Blood of Cancer Patients," *Clin. Cancer Res.* 9(2): 606-612 (2003).
Woo et al., "Regulatory CD4(+)CD25(+) T Cells in Tumors from Patients with Early-Stage Non-Small Cell Lung Cancer and Late-Stage Ovarian Cancer," *Cancer Res.* 61(12): 4766-4772 (2001).
Yang et al., "Overexpression of NBS1 Induces Epithelial-Mesenchymal Transition and Co-Expression of NBS1 and Snail Predicts Metastasis of Head and Neck Cancer," *Oncogene* 26(10): 1459-1467 (2007).
Yokoyama et al., "Expression and Functions of Snail in Acquiring High Invasive Ability in Sequamous Carcinoma Cells," *J. Jpn. Soc. Oral Tumors* 13(4):293-300 (2001) (English language abstract included).
English translation of Yokoyama et al., "Expression and Functions of Snail in Acquiring High Invasive Ability in Squamous Carcinoma Cells," *The Journal of the Japan Society for Oral Tumors* 13(4; Suppl.):293-300 (2001).
Zheng et al., "Natural and Induced CD4+CD25+ Cells Educate CD4+CD25− Cells to Develop Suppressive Activity: The Role of IL-2, TGF-beta, and IL-10," *J. Immunol.* 172(9): 5213-5221 (2004).
English Language Translation of the International Search Report for International Application No. PCT/JP2008/064987, mailed Dec. 2, 2008.
Abbadia et al., "Thrombospondin (TSP1) mediates in vitro proliferation of human MG-63 osteoblastic cells induced by alpha-thrombin," *FEBS Lett.* 329(3):341-6 (1993).
Fu et al., "TGF-beta induces Foxp3 + T-regulatory cells from CD4 + CD25—precursors," Am J Transplant. 4(10):1614-27 (2004).
Hasegawa et al., "Therapy for pneumonitis and sialadenitis by accumulation of CCR2—expressing CD4+CD25+ regulatory T cells in MRL/lpr mice," Arthritis Res Ther. 9(1):R15 (2007).
Tuszynski et al., "Biological activities of peptides and peptide analogues derived from common sequences present in thrombospondin, properdin, and malarial proteins," J Cell Biol. 116(1):209-17 (1992).

* cited by examiner

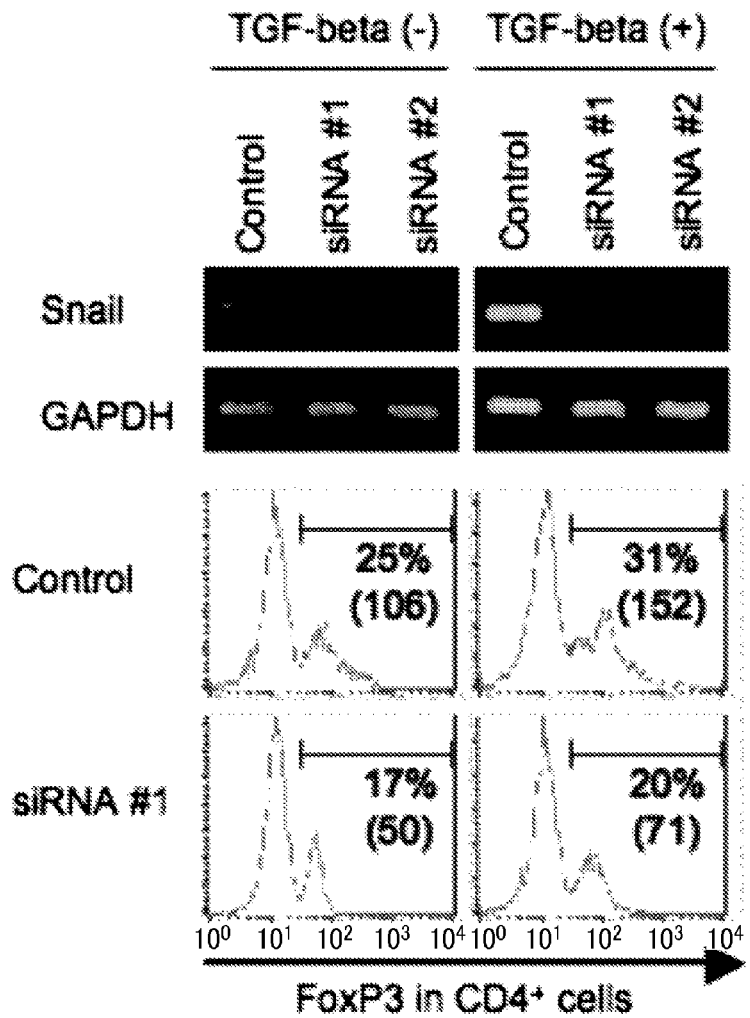

REDUCER OF IMMUNOSUPPRESSION BY TUMOR CELL AND ANTITUMOR AGENT USING THE SAME

CROSS-REFERENCE TO RELATED APPLICATIONS

This application is a continuation of U.S. patent application Ser. No. 12/674,881, having a 371(c) Date of Apr. 20, 2010, which is the U.S. National Stage filing under 35 U.S.C. §371 of International Application No. PCT/JP2008/064987, filed Aug. 22, 2008, which claims the benefit of Japanese Patent Application No. 2007-218977, filed Aug. 24, 2007.

TECHNICAL FIELD

The present invention is related to reducers of immunosuppression by tumor cells and antitumor agents using the same.

BACKGROUND ART

Regulatory T cells are known to play roles in the maintenance of self-tolerance and immunological homeostasis by suppressing immune responses both pathologically and physiologically (NPL 1).

For example, the cells which were initially CD4+CD25− are activated by stimulation with various factors to become CD4+CD25+ regulatory T cells, and eventually account for about 5 to 10% of peripheral CD4+ T cells. The CD4+CD25+ regulatory T cells start to express FoxP3 protein along with the differentiation of the CD4+ T cells (NPL 2, 3). Intercellular interactions as well as humoral factors such as TGF-beta (herein also referred to as TGF-b) and IL-10 have been shown to play important roles in this process (NPL 4).

The FoxP3 protein is considered to serve as a specific marker for the activation of regulatory T cells because its expression can be observed not only in CD4+CD25+ T cells but also in CD8+CD25+ T cells (NPL 5). Further, FoxP3 protein plays an important role in manifestation of functions of the regulatory T cell, because a naive T cell in which FoxP3 is forced to be expressed starts to show a phenotype like a regulatory T cell (NPL 6). Thus, FoxP3 gene is believed to be a master gene to regulate the differentiation and function of regulatory T cells (NPL 1).

The regulatory T cells are known to suppress immune responses (NPL 1) by exceptionally suppressing function of other cells (NPL 7). Its mechanism is yet to be known, but it has been suggested that the suppression of other cells functions is dependent on the intercellular interaction and that CTLA-4 is involved in the suppression (NPL 8). In particular, CTLA-4 was shown to be also involved in the differentiation of regulatory T cells (NPL 8).

While a host immunity is present in the body of a cancer patient to attack and eliminate the cancer, the cancer cells have a system to evade the defense by the host immunity. For example, it has been shown both in vitro and in vivo that the immune responses against cancer cells were changed when regulatory T cells were deleted in the presence of the cancer cells (NPL 17). Since increases in the number of regulatory T cells have been observed in stomach cancer (NPL 9, 10), rectal cancer (NPL 11), pancreatic cancer (NPL 12, 13), lung cancer (NPL 14) and glioma (NPL 17), they are considered to be involved in a system of the cancer cells to evade the immunity. However, its mechanism is yet to be known, and the way how the cytokines derived from the regulatory T cells affect the system is still a matter of controversy (NPL 17).

Since a deficiency in regulatory T cells causes severe autoimmune diseases (NPL 15), a mechanism common to the autoimmunity and the cancer immunity is considered to be present (NPL 16). The regulatory T cells are known to be involved in the suppression of immunological reactions to the cancer cells as well as the hyperimmune responses such as autoimmunity and allergic reactions through the suppression of immune responses (NPL 1).

CITATION LIST

Non Patent Literature

[NPL 1] Miyara and Sakaguchi Trends Mol. Med. 13, 108-116, 2007
[NPL 2] Fontenot et al. Nat. Immunol. 4, 330-336, 2003
[NPL 3] Fontenot et al. Immunity 22, 329-341, 2005
[NPL 4] Zheng et al. J. Immunol. 172, 5213-5221, 2004
[NPL 5] Bisikirska et al. J. Clin. Invest. 115, 2904-2913, 2005
[NPL 6] Hori et al. Science 299, 1057-1061, 2003
[NPL 7] Jiang and Chess J. Clin. Invest. 114, 1198-1208, 2004
[NPL 8] Atabani et al. Eur. J. Immunol. 35, 2157-2162, 2005
[NPL 9] Ichihara et al. Clin. Cancer Res. 9, 4404-4408, 2003
[NPL 10] Wolf et al. Clin. Cancer Res. 9, 606-612, 2003
[NPL 11] Hicky et al. Semin. Immunol. 11, 125-137, 1999
[NPL 12] Liyanage et al. J. Immunol. 169, 2756-2761, 2002
[NPL 13] Sasada et al. Cancer 98, 1098-1099, 2003
[NPL 14] Woo et al. Cancer Res. 61, 4766-4772, 2001
[NPL 15] Sakaguchi et al. Immunol. Rev. 182, 18-32, 2001
[NPL 16] Turk et al. Immunol. Rev. 188, 122-135, 2002
[NPL 17] Andaloussi and Lesniak Neuro-Oncology 8, 234-243, 2006

SUMMARY OF INVENTION

Technical Problem

A development of effective treatment for the diseases involving regulatory T cells is anticipated to be achieved by revealing the molecular mechanism of the immunosuppression by the regulatory T cells, thereby bringing it to a target of the treatment for the diseases involving regulatory T cells.

Accordingly, the present invention was made to provide the followings: a gene expression enhancer for enhancing expression of FoxP3 gene in a cell; a cell differentiation inducer for inducing differentiation of a cell into a regulatory T cell; an immunosuppressor for suppressing immunity and an agent for treating hyperimmune diseases based on the abovementioned actions; an inhibitor of enhancement of gene expression for inhibiting enhancement of FoxP3 gene expression in a cell; an inhibitor of induction of cell differentiation for inhibiting induction of differentiation of a cell into a regulatory T cell; a reducer of immunosuppression for reducing immunosuppression, a stimulator of tumor immunity and an antitumor agent based on the abovementioned actions; and the like.

Solution to Problem

Snail, a Zinc-finger transcription factor, is a malignant transformation factor of cancer, which has been known to progress as the expression of Snail becomes higher (Nature Rev Cancer 7, 415-428, 2007).

As a reason for this fact, it is considered that by suppressing expression of intercellular adhesion molecules such as E-cadherin, Snail regulates the epithelial-mesenchymal transition (EMT) which occurs during, for example, the processes of gastrulation and tissue/organ development in an ontogenesis, the repairing process when a normal tissue or cells are lost, and the metastatic process when cancer cells metastasize (Nature Rev Cancer 7, 415-428, 2007).

Thus, the inventors of the present invention endeavored to reveal the mechanism of malignant transformation of a cancer by Snail, and discovered by a forced expression of Snail in cultured cells that Snail protein enhances expression of MCP1 (monocyte chemoattractant protein-1) gene, TSP1 (thrombospondin-1) gene, FSTL1 (Follistatin-like 1) gene or IL-13Ra2 (interleukin 13 alpha 2 receptor) gene in a cancer cell, and that their gene products enhance the expression of FoxP3, a marker for activation of a regulatory T cell, in CD4+ T cells and CD8+ T cells, thereby accomplishing the present invention.

Accordingly, the embodiments of the present invention are as follows.

(1) A gene expression enhancer for enhancing expression of FoxP3 gene in a cell, wherein the enhancer activates MCP1 signaling in the cell.
(2) A gene expression enhancer for enhancing expression of FoxP3 gene in a cell, containing a cell expressing a Snail protein, an MCP1 protein, an FSTL1 protein, a membrane IL-13Ra2 protein or a secretory IL-13Ra2 protein.
(3) A gene expression enhancer for enhancing expression of FoxP3 gene in a cell, comprising an MCP1 protein, an FSTL1 protein or a secretory IL-13Ra2 protein.
(4) The gene expression enhancer according to (3), comprising a culture supernatant of a cell expressing a Snail protein or a cell secreting an MCP1 protein, an FSTL1 protein or a secretory IL-13Ra2 protein.
(5) The gene expression enhancer according to (2) or (4), wherein the cell is a tumor cell.
(6) A cell differentiation inducer for inducing differentiation of a cell into a regulatory T cell, wherein the inducer activates MCP1 signaling in the cell.
(7) A cell differentiation inducer for inducing differentiation of a cell into a regulatory T cell, containing a cell expressing a Snail protein, an MCP1 protein, an FSTL1 protein, a membrane IL-13Ra2 protein or a secretory IL-13Ra2 protein.
(8) A cell differentiation inducer for inducing differentiation of a cell into a regulatory T cell, comprising an MCP1 protein, an FSTL1 protein or a secretory IL-13Ra2 protein.
(9) An immunosuppressor, wherein the immunosuppressor activates MCP1 signaling.
(10) An immunosuppressor comprising a cell expressing a Snail protein or a cell expressing an MCP1 protein, an FSTL1 protein, a membrane IL-13Ra2 protein or a secretory IL-13Ra2 protein.
(11) An immunosuppressor comprising an MCP1 protein, an FSTL1 protein or a secretory IL-13Ra2 protein.
(12) An agent for treating hyperimmune disease, wherein the agent activates MCP1 signaling.
(13) An agent for treating hyperimmune disease comprising a cell expressing a Snail protein, an MCP1 protein, an FSTL1 protein, a membrane IL-13Ra2 protein or a secretory IL-13Ra2 protein.
(14) An agent for treating hyperimmune disease comprising an MCP1 protein, an FSTL1 protein or a secretory IL-13Ra2 protein.
(15) An inhibitor of enhancement of gene expression for inhibiting enhancement of expression of FoxP3 gene in a cell, wherein the inhibitor suppresses MCP1 signaling in the cell.
(16) An inhibitor of enhancement of gene expression for inhibiting enhancement of expression of FoxP3 gene in a cell, wherein the inhibitor suppresses function of an MCP1 protein, an FSTL1 protein, a membrane IL-13Ra2 protein or a secretory IL-13Ra2 protein.
(17) The inhibitor of enhancement of gene expression according to (15) or (16), comprising an anti-MCP1 antibody with MCP1 inhibiting activity.
(18) The inhibitor of enhancement of gene expression according to (16), comprising an anti-FSTL1 antibody with FSTL1 protein inhibiting activity, an anti-membrane IL-13Ra2 antibody with membrane IL-13Ra2 protein inhibiting activity or an anti-secretory IL-13Ra2 antibody with secretory IL-13Ra2 protein inhibiting activity.
(19) An inhibitor of induction of cell differentiation for inhibiting induction of differentiation of a cell into a regulatory T cell, wherein the inhibitor suppresses MCP1 signaling in the cell.
(20) An inhibitor of induction of cell differentiation for inhibiting induction of differentiation of a cell into a regulatory T cell, wherein the inhibitor suppresses function of an MCP1 protein, an FSTL1 protein, a membrane IL-13Ra2 protein or a secretory IL-13Ra2 protein.
(21) The inhibitor of induction of cell differentiation according to (19) or (20), comprising an anti-MCP1 antibody with MCP1 inhibiting activity.
(22) The inhibitor of induction of cell differentiation according to (20), comprising an anti-FSTL1 antibody with FSTL1 protein inhibiting activity, an anti-membrane IL-13Ra2 antibody with membrane IL-13Ra2 protein inhibiting activity or an anti-secretory IL-13Ra2 antibody with secretory IL-13Ra2 protein inhibiting activity.
(23) A reducer of immunosuppression suppressing MCP1 signaling.
(24) A reducer of immunosuppression suppressing function of an MCP1 protein, an FSTL1 protein, a membrane IL-13Ra2 protein or a secretory IL-13Ra2 protein.
(25) A stimulator of tumor immunity suppressing MCP1 signaling.
(26) A stimulator of tumor immunity suppressing function of an MCP1 protein, an FSTL1 protein, a membrane IL-13Ra2 protein or a secretory IL-13Ra2 protein.
(27) An antitumor agent suppressing MCP1 signaling.
(28) An antitumor agent, wherein the agent suppresses function of an MCP1 protein, an FSTL1 protein, a membrane IL-13Ra2 protein or a secretory IL-13Ra2 protein.
(29) A suppressor of tumor growth, wherein the suppressor suppresses MCP1 signaling or function of a TSP1 protein.
(30) A suppressor of tumor cell infiltration, wherein the suppressor suppresses MCP1 signaling or function of an FSTL1 protein.
(31) A suppressor of tumor metastasis, wherein the suppressor suppresses MCP1 signaling or function of an FSTL1 protein.
(32) A gene expression enhancer of FoxP3 gene, MCP1 (monocyte chemoattractant protein-1) gene, TSP1 (thrombospondin-1) gene, FSTL1 (Follistatin-like 1) gene or IL-13Ra2 (interleukin 13 alpha 2 receptor) gene in a cell, comprising a substance enhancing Snail activity.
(33) The gene expression enhancer according to (32), wherein the substance enhancing Snail protein activity is an expression vector of a snail gene.
(34) The gene expression enhancer according to (32), wherein the cell is a Panc-1 cell.
(35) An anticancer agent for blood cancer, comprising an inhibitory substance inhibiting function of a Snail protein.
(36) The anticancer agent according to (35), wherein the inhibitory substance inhibits expression of the snail gene.

(37) The anticancer agent according to (35) or (36), wherein the blood cancer is leukemia.
(38) A gene expression enhancing method for enhancing expression of FoxP3 gene in a cell, comprising the step of activating MCP1 signaling in the cell.
(39) A gene expression enhancing method for enhancing expression of FoxP3 gene in a cell, comprising the step of allowing the cell to contact with a cell expressing one or more proteins selected from the group consisting of a Snail protein, an MCP1 protein, an FSTL1 protein, a membrane IL-13Ra2 protein and a secretory IL-13Ra2 protein.
(40) The gene expression enhancing method according to (39), wherein the cell is a tumor cell.
(41) A gene expression enhancing method for enhancing expression of FoxP3 gene in a cell, comprising the step of allowing the cell to contact with one or more proteins selected from the group consisting of a Snail protein, an MCP1 protein, an FSTL1 protein, a membrane IL-13Ra2 protein and a secretory IL-13Ra2 protein.
(42) The gene expression enhancing method for enhancing expression of FoxP3 gene in a cell according to (40), comprising the step of allowing the cell to contact with a culture supernatant of a cell expressing one or more proteins selected from the group consisting of a Snail protein, an MCP1 protein, an FSTL1 protein, a membrane IL-13Ra2 protein and a secretory IL-13Ra2 protein.
(43) The gene expression enhancing method according to (42), wherein the cell is a tumor cell.
(44) A cell differentiation inducing method for inducing differentiation of a cell into a regulatory T cell, comprising the step of activating MCP1 signaling in the cell.
(45) A cell differentiation inducing method for inducing differentiation of a cell into a regulatory T cell, comprising the step of allowing the cell to contact with a cell expressing a Snail protein, an MCP1 protein, an FSTL1 protein, a membrane IL-13Ra2 protein or a secretory IL-13Ra2 protein.
(46) A cell differentiation inducing method for inducing differentiation of a cell into a regulatory T cell, comprising the step of allowing the cell to contact with an MCP1 protein, an FSTL1 protein or a secretory IL-13Ra2 protein.
(47) A method for treating a patient with hyperimmunity, comprising the step of administering to the patient an activator to activate MCP1 signaling.
(48) A method for treating a patient with hyperimmunity, comprising the step of administering to the patient a cell expressing a Snail protein or a cell expressing an MCP1 protein, an FSTL1 protein, a membrane IL-13Ra2 protein or a secretory IL-13Ra2 protein.
(49) A method for treating a patient with hyperimmunity, comprising the step of administering to the patient an MCP1 protein, an FSTL1 protein or a secretory IL-13Ra2 protein.
(50) An agent for treating hyperimmune disease activating MCP1 signaling.
(51) A gene expression enhancement-inhibiting method for inhibiting enhancement of FoxP3 gene expression in a cell, comprising the step of suppressing MCP1 signaling in the cell.
(52) A gene expression enhancement-inhibiting method for inhibiting enhancement of FoxP3 gene expression in a cell, comprising the step of suppressing function of an MCP1 protein, an FSTL1 protein, a membrane IL-13Ra2 protein or a secretory IL-13Ra2 protein in the cell.
(53) The gene expression enhancement-inhibiting method according to (51), wherein the cell is allowed to contact with an anti-MCP1 antibody with MCP1 inhibiting activity.
(54) The gene expression enhancement-inhibiting method according to (52), wherein the cell is allowed to contact with an anti-FSTL1 antibody with FSTL1 protein inhibiting activity, an anti-membrane IL-13Ra2 antibody with membrane IL-13Ra2 protein inhibiting activity or an anti-secretory IL-13Ra2 antibody with secretory IL-13Ra2 protein inhibiting activity.
(55) A cell differentiation induction-inhibiting method for inhibiting induction of differentiation of a cell into a regulatory T cell, comprising the step of suppressing MCP1 signaling in the cell.
(56) A cell differentiation induction-inhibiting method for inhibiting induction of differentiation of a cell into a regulatory T cell, comprising the step of suppressing function of an MCP1 protein, an FSTL1 protein, a membrane IL-13Ra2 protein or a secretory IL-13Ra2 protein in the cell.
(57) The cell differentiation induction-inhibiting method according to (55), wherein the cell is allowed to contact with an anti-MCP1 antibody with MCP1 inhibiting activity.
(58) The cell differentiation induction-inhibiting method according to (56), wherein the cell is allowed to contact with an anti-FSTL1 antibody with FSTL1 protein inhibiting activity, an anti-membrane IL-13Ra2 antibody with membrane IL-13Ra2 protein inhibiting activity or an anti-secretory IL-13Ra2 antibody with secretory IL-13Ra2 protein inhibiting activity.
(59) An immunosuppression reducing method for reducing immunosuppression of a patient with suppressed immunity, comprising the step of suppressing MCP1 signaling in the patient.
(60) An immunosuppression reducing method for reducing immunosuppression of a patient with suppressed immunity, comprising the step of suppressing function of an MCP1 protein, an FSTL1 protein, a membrane IL-13Ra2 protein or a secretory IL-13Ra2 protein in the patient.
(61) A method for stimulating tumor immunity in a patient with suppressed tumor immunity, comprising the step of suppressing MCP1 signaling in the patient.
(62) A method for stimulating tumor immunity in a patient with suppressed tumor immunity, comprising the step of suppressing function of an MCP1 protein, an FSTL1 protein, a membrane IL-13Ra2 protein or a secretory IL-13Ra2 protein.
(63) A method for treating a tumor patient, including the step of suppressing MCP1 signaling in the patient.
(64) A method for treating a tumor patient, including suppressing function of an MCP1 protein, an FSTL1 protein, a membrane IL-13Ra2 protein or a secretory IL-13Ra2 protein in the patient.
(65) A method for treating a tumor patient, comprising suppressing function of a TSP1 protein in the patient.
(66) A gene expression enhancing method for FoxP3 gene, MCP1 (monocyte chemoattractant protein-1) gene, TSP1 (thrombospondin-1) gene, FSTL1 (Follistatin-like 1) gene or IL-13Ra2 (interleukin 13 alpha 2 receptor) gene in a cell, comprising the step of allowing the cell to contact with a substance for enhancing Snail protein activity.
(67) The gene expression enhancing method according to (66), wherein the substance for enhancing Snail protein activity is a snail gene expression vector.
(68) The gene expression enhancing method according to (66), wherein the cell is a Panc-1 cell.
(69) A method for treating a patient with blood cancer, comprising the step of administering to the patient a substance for inhibiting function of a Snail protein.
(70) The treating method according to (69), wherein the substance inhibits expression of snail gene.

(71) The treating method according to (69), wherein the blood cancer is leukemia.

BRIEF DESCRIPTION OF DRAWINGS

FIG. 1 is a table showing phenotypes of the Panc-1 cells in which snail gene is forced to be expressed in one example of the present invention.

FIG. 2A shows induction of expression of FoxP3 in CD4+ cells by coculturing PBMCs with the Hs294T cells treated with TGF-beta in one example of the present invention.

DESCRIPTION OF EMBODIMENTS

Figure 2B:
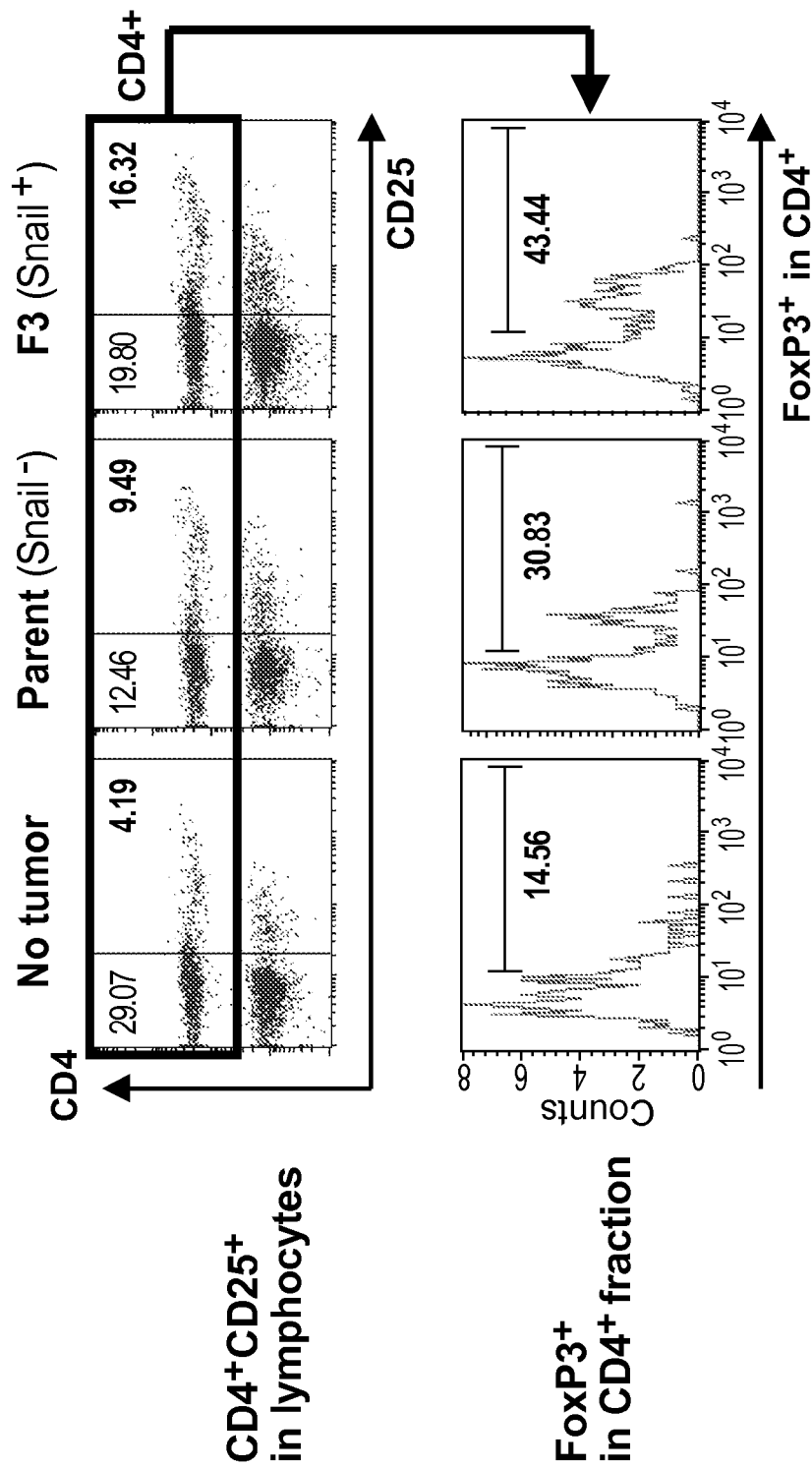
FIG. 2B shows the induction of expression of FoxP3 in CD4+ cells by coculturing PBMCs with Panc-1 cells or F3 cells in one example of the present invention.

Hereinafter the embodiments of the present invention thus accomplished based on the abovementioned findings are described in detail by giving examples. Where no explanation is given in the embodiments or examples, methods described in standard protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); and F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., as well as their modifications/variations, are employed. Where a commercially available reagent kit or a measuring instrument is used, the protocol attached thereto will be followed.

It is to be understood that the object, characteristics, and advantages of the present invention as well as the ideas thereof will be apparent to those skilled in the art from the descriptions given herein, and the present invention can be easily reproduced by those skilled in the art based on the descriptions given herein. The embodiments and specific examples of the invention described herein are to be taken as preferred embodiments of the present invention, and these descriptions are presented only for illustrative and/or explanatory purposes. Therefore, the present invention is not limited to these examples, and all the embodiments those skilled in the art can assume from the examples are also encompassed by the present invention. It is further apparent to those skilled in the art that various changes and modifications may be made based on the descriptions given herein within the intent and scope of the present invention disclosed herein, and such variations and modifications are also encompassed by the present invention.

==Gene Expression Enhancer I. Genes of MCP1, TSP1, FSTL1 and IL-13Ra2==

The gene expression enhancer for enhancing expression of MCP1 (monocyte chemoattractant protein-1) gene, TSP1 (thrombospondin-1) gene, FSTL1 (Follistatin-like 1) gene or IL-13Ra2 (interleukin 13 alpha 2 receptor) gene in the cells to be treated according to the present invention may contain a substance for enhancing Snail protein activity.

The substance for enhancing Snail protein activity may be any of substances that enhances the intrinsic activity of a Snail protein molecule, as well as any of substances that enhances overall Snail protein activity in a cell, and the examples include expression vectors of NBS1 which provide an enhancement of expression of Snail protein (Yang et al. Oncogene, 26, 1459-1467, 2007), expression vectors of snail gene, and the like.

The method for using the gene expression enhancer may be chosen in accordance with the characteristics of the substance for enhancing Snail protein activity as an effective ingredient. An administration of the substance from outside of the cells to be treated should be chosen when it acts on the membrane of the cells, whereas an introduction of the substance into the cell should be chosen when the substance acts inside the cell.

While the cells to be treated by the enhancement of gene expression are not particularly limited, the preferred examples are tumor cells, in particular Panc-1 cell.

==Gene Expression Enhancer II. FoxP3 Gene==

The gene expression enhancer for enhancing the expression of FoxP3 gene in the cells to be treated according to the present invention may contain a substance for enhancing Snail protein activity.

The substance for enhancing Snail activity may be any of substances that enhances the intrinsic activity of a Snail protein molecule, as well as any of substances that enhances overall Snail protein activity in the cell, and the examples include the expression vectors for NBS1 that enhance the Snail expression (Yang et al. Oncogene, 26, 1459-1467, 2007), the expression vectors for snail gene, and the like.

In a method for using the gene expression enhancer, a cell in which the Snail activity has been enhanced by the substance for enhancing Snail activity, or the culture supernatant of the cell, may be administered to the cells to be treated to enhance the expression of FoxP3 gene. In an example, both cells may be co-cultured in vivo or in vitro. If the cells to be treated are located in a living body, the cell with the enhanced Snail protein activity or its culture supernatant may be injected to the vicinity of the cells to be treated.

While the cells to be treated are not particularly limited, the preferred examples are T cells, and more preferred are naive T cells, CD4+ T cells and CD8+ T cells.

==Gene Expression Enhancer III. FoxP3 Gene==

The gene expression enhancer for enhancing the expression of FoxP3 gene in the cells to be treated according to the present invention may activate the MCP1 signaling in the cells to be treated and/or in other cells that coexist with the cells to be treated.

The effective ingredient to be contained in the gene expression enhancer may be, for example, cells expressing Snail protein, cells expressing MCP1, MCP1 protein or MCP1 receptor activating substance, and more specifically tumor cells secreting MCP1, cells to which an expression vector for MCP1 gene has been introduced, culture supernatants of cells secreting MCP1 protein, purified MCP1 protein, anti-MCP1 receptor antibody which activates MCP1 receptor, and the like.

The gene expression enhancer for enhancing the expression of FoxP3 gene in the cells to be treated according to the present invention may contain a cell expressing Snail protein, FSTL1 protein, membrane IL-13Ra2 protein or secretory IL-13Ra2 protein, the FSTL1 protein or the secretory IL-13Ra2 protein.

Specific examples that may be used as the gene expression enhancer include tumor cells expressing Snail protein, FSTL1 protein, membrane IL-13Ra2 protein or secretory IL-13Ra2 protein, cells to which an expression vector for the gene encoding Snail, FSTL1, membrane IL-13Ra2 or secretory IL-13Ra2 has been introduced, culture supernatants of cells expressing Snail protein, culture supernatants of cells secreting FSTL1 protein or secretory IL-13Ra2 protein, purified FSTL1 proteins, and the secretory IL-13Ra2 proteins.

The gene expression enhancer may contain one or more than one of the abovementioned substances.

In a method for using the gene expression enhancer, the enhancer may be, for example, directly administered to the cells to be treated. In this case, another cell may coexist, and the preferred examples of the cell to coexist are antigen-presenting cells such as dendritic cells and macrophages that can induce proliferation of T cells by presenting antigens. Alternatively, the gene expression enhancer may be administered to cells other than the cells to be treated, and then culture supernatants of this cell may be administered to the cells to be treated. The cell to be used in this case is preferably antigen-presenting cells such as dendritic cells or macrophages.

While the cells to be treated are not particularly limited, the preferred examples are T cells, and more preferred are naive T cells, CD4+ T cells or CD8+ T cells.

==Cell Differentiation Inducer, Immunosuppressor==

FoxP3 is a master gene to regulate the differentiation and function of regulatory T cells which possess the function of immunosuppression (Miyara and Sakaguchi Trends Mol. Med. 13, 108-116, 2007; Hori et al. Science 299, 1057-1061, 2003; Jiang and Chess J. Clin. Invest. 114, 1198-1208, 2004). Therefore, the abovementioned gene expression enhancer for enhancing the expression of FoxP3 gene can be used as a cell differentiation inducer for inducing differentiation of the cells to be treated into regulatory T cells, as well as an immunosuppressor. Indeed, the fact that the FoxP3 gene expression enhancer which contains cells expressing snail gene can provide cocultured CD4+ cells with the proliferation suppressing capability against T cells also indicates that the gene expression enhancer for FoxP3 can be used as a cell differentiation inducer as well as an immunosuppressor.

While the cells to be treated are not particularly limited, the preferred examples are T cells, and more preferred are naive T cells, CD4+ T cells or CD8+ T cells. The cell differentiation inducer and the immunosuppressor may be used either in vivo or in vitro. The immunosuppressor may suppress hyperimmunity and/or normal immunity.

==Agent for Treating Hyperimmune Disease==

Hypofunction of regulatory T cells causes hyperimmune diseases such as autoimmunity and allergic diseases (Miyara and Sakaguchi Trends Mol. Med. 13, 108-116, 2007; Turk et al. Immunol. Rev. vol. 188, p. 122-135, 2002). Therefore, these hyperimmune diseases can be treated by inducing differentiation of the T cells to be treated into regulatory T cells, thereby suppressing immunity. Accordingly, the abovementioned cell differentiation inducer as well as the immunosuppressor can be used as an agent for treating hyperimmune diseases to treat autoimmunity, allergic diseases and the like. A hyperimmune disease as used herein means a disease caused by the hypofunction of regulatory T cells, including but not limited to autoimmunity and allergic diseases. While the cells to be treated are not particularly limited, the preferred examples are T cells, and more preferred are naive T cells, CD4+ T cells or CD8+ T cells.

While the method for using the agent for treating hyperimmune diseases may be chosen appropriately, the agent is preferably administered to patients by either a systemic administration or a topical administration to the site of hyperimmunity.

==Inhibitor of Enhancement of FoxP3 Gene Expression==

The inhibitor of enhancement of FoxP3 gene expression for inhibiting the enhancement of expression of FoxP3 gene in the cells to be treated according to the present invention may suppress MCP1 signaling in the cells to be treated and/or cells coexisting with the cells to be treated.

The effective ingredient to be contained in the inhibitor of enhancement of gene expression may suppress function of, for example, MCP1 protein or MCP1 receptor, and the specific examples include inhibitory antibodies to inhibit the function, hybridomas secreting the inhibitory antibodies, small compounds with the inhibiting activity, and the like.

The inhibitor of enhancement of FoxP3 gene expression according to the present invention may also suppress function of FSTL1 protein, membrane IL-13Ra2 protein or secretory IL-13Ra2 protein.

The effective ingredient to be contained in the inhibitor of enhancement of gene expression may be, for example, anti-FSTL1 antibody with FSTL1 protein inhibiting activity, anti-membrane IL-13Ra2 antibody with membrane IL-13Ra2 protein inhibiting activity or anti-secretory IL-13Ra2 antibody with secretory IL-13Ra2 protein inhibiting activity.

In a method for using the inhibitor of enhancement of gene expression, the inhibitor may be administered in vivo or in vitro to the cells to be treated or its vicinity. In the case where the inhibitor of enhancement of FoxP3 gene expression exerts its effect by suppressing MCP1 signaling in a cell which coexists with the cells to be treated by inhibiting the enhancement of expression of FoxP3 gene, the inhibitor of enhancement of gene expression is administered so that it can act on the coexisting cells. The coexisting cells are preferably antigen-presenting cells, such as dendritic cells or macrophages.

While the cells to be treated are not particularly limited, the preferred examples are T cells, and more preferred are naive T cells, CD4+ T cells or CD8+ T cells.

==Inhibitor of Induction of Cell Differentiation, Reducer of Immunosuppression==

As mentioned above, FoxP3 is a master gene to regulate differentiation and function of regulatory T cells that possess function of immunosuppression (Miyara and Sakaguchi Trends Mol. Med. 13, 108-116, 2007; Hori et al. Science 299, 1057-1061, 2003; Jiang and Chess J. Clin. Invest. 114, 1198-1208, 2004). Therefore, by suppressing the enhancement of expression of FoxP3, an induction of differentiation of the cells to be treated into regulatory T cells can be inhibited, and in turn, an immunosuppression by the regulatory T cell can be reduced. Thus, the abovementioned inhibitor of enhancement of gene expression for suppressing the enhancement of expression of FoxP3 gene can be used as an inhibitor of induction of cell differentiation for inhibiting induction of differentiation of the cells to be treated into regulatory T cells, as well as a reducer of immunosuppression.

In a method for using the inhibitor of induction of cell differentiation or the reducer of immunosuppression, the inhibitor or reducer may be administered in vivo or in vitro to the cells to be treated by inhibiting the induction of differentiation into regulatory T cells, or to the vicinity of the cells to be treated. In the case where the inhibitor of induction of cell differentiation or the reducer of immunosuppression exerts its effect by suppressing MCP1 signaling in cells which coexist with the cells to be treated, the inhibitor or the reducer is administered so that it can act on the coexisting cells. The coexisting cells are preferably antigen-presenting cells, such as dendritic cells or macrophages.

While the cells to be treated are not particularly limited, the preferred examples are the T cells, and more preferred are naive T cells, CD4+ T cells or CD8+ T cells. The inhibitor of induction of cell differentiation and the reducer of immunosuppression may be used either in vivo or in vitro.

==Stimulator of Tumor Immunity, Antitumor Agent==

The inventors of the present invention discovered that Snail protein enhances expression of MCP1 gene, TSP1 gene, FSTL1 gene and IL-13Ra2 gene in tumor cells, and that their gene products act directly or indirectly on CD4+ T cells or CD8+ T cells to enhance the expression of FoxP3, a marker for activation of regulatory T cells. Namely, it was discovered that tumor cells suppress the tumor immunity of their host by acting on the surrounding immune cells via mediating proteins for suppression of tumor immunity such as MCP1 protein, TSP1 protein, FSTL1 protein, IL-13Ra2 protein, IL-13 protein, IL-4 protein, CCR2 protein and IL-10 protein, thereby inducing differentiation of the immune cells into regulatory T cells. Based on this fact, the inhibitor of enhancement of FoxP3 gene expression according to the present invention, which inhibits the action of these mediating proteins, can reduce the suppression of tumor immunity by tumor cells, thereby stimulating the tumor immunity. The stimulation of the patient's own tumor immunity can bring a therapeutic effect against the tumor in the patient. Therefore, the inhibitor of enhancement of FoxP3 gene expression according to the present invention can be used as a stimulator of tumor immunity as well as an antitumor agent. Examples of the inhibitory substances for inhibiting function of the mediating protein for suppression of tumor immunity include antibodies and competitive inhibitory molecules such as dominant-negative mutants against the mediating protein for suppression of tumor immunity.

Indeed, tumor cells are usually digested and eliminated via phagocytosis by phagocytes including the antigen-presenting cells such as dendritic cells, but Snail-expressing tumor cells inhibit the phagocytosis. However, the inhibitory substance for inhibiting the action of the mediating proteins can suppress the inhibition of phagocytosis by the Snail-expressing tumor cells.

While the method for using the stimulator of tumor immunity and the antitumor agent may be chosen appropriately, they are preferably administered to patients by a topical administration to the site of the tumor or its vicinity.

==Suppressor of Tumor Growth==

The suppressor of tumor growth according to the present invention may suppress the proliferation of tumor cells by suppressing MCP1 signaling or function of TSP1 protein. The suppressor of tumor growth may contain as an effective ingredient, for example, an inhibitory antibody for inhibiting function of MCP1 protein, MCP1 receptor or TSP1 protein, or a hybridoma secreting the inhibitory antibody.

While the method for using the suppressor of tumor growth may be appropriately chosen, it is preferably administered to patients by either systemic administration or topical administration to the site of the tumor or its vicinity.

==Suppressor of Tumor Cell Infiltration, Suppressor of Tumor Metastasis==

The suppressor of tumor cell infiltration according to the present invention may suppress infiltration of tumor cells by suppressing MCP1 signaling or function of FSTL1 protein.

During the metastasis of tumor cells, they infiltrate between normal cells or cells forming vascular walls. Therefore, metastasis of tumors can be suppressed by suppressing the infiltration of tumor cells. Accordingly, the suppressor of tumor cell infiltration can be used as a suppressor of tumor metastasis.

The suppressor of tumor cell infiltration and the suppressor of tumor metastasis according to the present invention may contain as an effective ingredient, for example, an inhibitory antibody for inhibiting function of MCP1 protein, MCP1 receptor or FSTL1 protein, a hybridoma secreting the inhibitory antibody or a dominant-negative mutant of MCP1 (7ND).

While the method for using the suppressor of tumor metastasis may be appropriately chosen, it is preferably administered to patients by either systemic administration or topical administration to the site of the tumor or its vicinity.

With regard to any of the abovementioned agents according to the present invention, the tumor to be treated is not particularly limited, and it may be either a solid cancer or a blood cancer, and may be either an epithelial cancer or any other type of malignant cancer.

==Anticancer Agent for Blood Cancer==

The anticancer agent for blood cancers according to the present invention may contain an inhibitory substance for inhibiting Snail function. The inhibitory substance for inhibiting Snail function as used herein means a small compound or a protein (such as a dominant-negative mutant) which inhibits intrinsic activity of the Snail protein molecule, as well as any of substances that inhibits overall function of Snail protein in the cell, and the examples include nucleic acids (antisense RNA, siRNA, shRNA, etc.) which inhibit the expression of Snail protein, expression vectors for these nucleic acids, and competitive inhibitory proteins. The anticancer agent preferably exerts its function by inhibiting the infiltration of malignantly-transformed blood cells.

It should be noted that the relation of Snail with the blood cancer has never been known beforehand. Even if the involvement of the expression of Snail in the metastasis of cancers might have been imagined, it was due to the regulation of intercellular adhesion molecules such as E-cadherin found in the solid cancer, and the involvement of Snail in cancers of blood cells in a suspension state has never been obvious by those skilled in the art.

While the blood cancers are not particularly limited, the examples include leukemia, malignant lymphoma and multiple myeloma.

EXAMPLES

{1} Forced Expression of Snail Gene in Panc-1 Cell

<Purpose>

Cell clones D6, D10, F3 and F5 having enhanced expression of Snail were obtained from Panc-1 cell, a strain of human pancreatic cancer cell, by forced expression of snail gene, and their phenotypes were examined with regard to cellular shape, expression levels of mRNA and protein of Snail and E-cadherin, cellular growth capability, cellular adhesion capability, cellular mobility and cellular infiltration capability.

<Experimental Methods>

(1) Construction of Expression Vector for Snail Gene and Introduction of the Vector A snail cDNA (CDS 71-865, 795 bp) was amplified by PCR from the Panc-1 cell which had been stimulated by TGF-beta, known as one of the inducers for EMT, and was inserted into an EcoR I-Xho I restriction site of a pcDNA3.1 (+) plasmid vector (Invitrogen) having a G418 resistance gene. The vector was then introduced into a tumor cell strain by electroporation, and after 2 weeks of culturing, cells that acquired drug resistance were selected using G418 (2 mg/mL) and cloned.

(2) Analysis of Gene Expression in Snail Gene-Introduced Cell Line by RT-PCR

RNAs were extracted from the human tumor cell lines by using RNeasy (QIAGEN) and reverse-transcribed by using AMV (incubated at 42° C. for 50 min and at 70° C. for 15 min), and cDNAs thus obtained were used in the following PCR (iCycler, BIO-RAD). The sequences of primers for snail cDNA were as follows.

```
                                           (SEQ ID NO: 1)
     Forward       5'-CAGATGAGGACAGTGGGAAAGG-3'

(SEQ ID NO: 2)
     Reverse       5'-ACTCTTGGTGCTTGTGGAGCAG-3'
```

(3) Analysis of Protein Expression in Snail Gene-Introduced Cell Line by Immunohistochemical Staining In order to examine the expression levels of proteins in the tumor cells, the tumor cells ($5 \times 10^4$ cells) were cultured in slide chambers overnight (37° C., 5% $CO_2$), and then fixed with 4% paraformaldehyde. After blocking of non-specific staining with using normal goat serum, cells were treated with Cytofix/Cytoperm (BD Phermingen) for intracellular staining (4° C., 20 min), then stained with various antibodies (e.g. an anti-Snail antibody (SANTA CRUZ) plus an Alexa488-labeled anti-goat IgG (Molecular Probes), or an anti-E-cadherin antibody (BD Bioscience) plus an Alexa568-labeled anti-mouse IgG (Molecular Probes)), for 1 hour at 4° C. Afterwards, cells were mounted with using Vecter Shield (Vector Laboratories), and observed under a fluorescence microscope (LSM 5 PASCAL, Carl Zeiss).

<Results>

FIG. 1A summarizes the phenotypes of the cell lines introduced with snail gene.

While intrinsic expression of Snail protein was observed in the Panc-1 cell as the parent cell line, the expression level of Snail protein was further increased by the introduction of the expression vector for snail gene in the clones listed in the table. As the results, in each of the clones, the cellular shape was changed from round shape to spindle/spreading shape, the cellular growth capability ("Proliferation") was reduced both in vitro and in vivo, the protein level of E-cadherin as well as the cellular adhesion capability ("Adhesion") were reduced, and the cellular mobility ("Migration") as well as the cellular infiltration capability ("Invasion") were increased. In particular, a prominent effect was observed in Clone F3 with regard to the epithelial-mesenchymal transition (EMT), and thus F3 was used in the following Examples.

{2} Induction of Expression of FoxP3 in CD4+ Cells by Coculturing with Hs294T Cells <Purpose>

By coculturing human melanoma Hs294T cells treated by TGF-beta with PBMCs, it will be shown that an enhancement of expression of FoxP3 protein occurs in CD4+ cells among PBMCs and that the expression of FoxP3 protein disappears by a knockdown of snail gene.

<Experimental Methods>

(1) TGF-Beta Treatment of Tumor Cells

The following oligonucleotides of either the snail gene-specific siRNAs (Invitrogen) or their scrambled sequences as a negative control were added to the culture media for culturing human melanoma Hs294T cells in a 6-well plate at 2 µg/$3 \times 10^5$/2 mL, and the cells were cultured for 2 days. The cells were then washed, added with TGF-beta (5 ng/mL), and cultured for 3 more days.

```
Sequences of snail gene-specific siRNAs #1:
                                          (SEQ ID NO: 3)
Forward         5'- GCGAGCUGCAGGACUCUAA-3'

(SEQ ID NO: 4)
Reverse         5'- UUAGAGUCCUGCAGCUCGC-3'

Sequences of snail gene-specific siRNAs #2:
                                          (SEQ ID NO: 5)
Forward         5'- CCCACUCAGAUGUCAAGAA-3'

(SEQ ID NO: 6)
Reverse         5'- UUCUUGACAUCUGAGUGGG-3'

Sequences of siRNA control:
                                          (SEQ ID NO: 7)
Forward         5'-GCGCGUCAGGACUCGAUAA-3'

(SEQ ID NO: 8)
Reverse         5'-UUAUCGAGUCCUGACGCGC-3'
```

(2) Analysis of Gene Expression by RT-PCR in Tumor Cell

The tumor cells were recovered and the expression of snail gene was measured by RT-PCR according to {1} above. The expression of GAPDH gene as a control for quantifying the expression was also measured by using the following primers.

```
                                          (SEQ ID NO: 9)
Forward         5'- GTCAACGGATTTGGTCGTATT-3'

(SEQ ID NO: 10)
Reverse         5'- ATCACTGCCACCCAGAAGACT-3'
```

(3) Isolation of Human Peripheral Blood Cell (PBMC)

A blood obtained from a healthy individual was added with 1/10 volume of 4% sodium citrate, overlaid on Ficoll (specific gravity of 1.090) and centrifuged (1500 rpm, 20 min, room temperature), and a fraction of cells present in the interphase was used as "(bulk) PBMCs".

(4) Coculture of PBMC with Tumor Cell (Hs294T Cell)

The tumor cells obtained as above were first inactivated by either a treatment with MMC (100 μg/mL, 2 hours at 37° C.) or an irradiation of X-ray (20K rad). The PBMCs were seeded and cocultured in a plate along with the tumor cells at a ratio of 1:10 (for example, $1 \times 10^5$ of PBMCs and $1 \times 10^4$ tumor cells in a 96-well plate, or $5 \times 10^5$ of PBMCs and $5 \times 10^4$ of tumor cells in a 24-well plate) at 37° C. in 5% $CO_2$ for 3 to 5 days, and then the PBMCs were recovered.

(5) Expression Analysis of FoxP3 Protein

The PBMCs thus obtained were first incubated with a commercially available anti-CD4 antibody (BD PharMingen) and an anti-CD25 antibody (BD PharMingen) for 1 hour. Afterwards, the cells were treated with Cytofix/Cytoperm (BD Pharmingen) for intracellular staining (4° C., 20 min), then incubated with an anti-FoxP3 antibody (eBioscience) at 4° C. for 1 hour, and subjected to a FACScan flow cytometer (Becton Dickinson) with gating set for CD4+ or CD4+CD25+ cell fraction to analyze the expression level of FoxP3.

<Results>

FIG. 2A shows the results of the analysis for the expression of snail gene and the expression of FoxP3. While the expression of snail gene was increased in the human melanoma Hs294T cells by treating with TGF-beta ("Control" in the figure), the expression was suppressed by the snail gene-specific siRNAs. The content of the cells expressing FoxP3 in the CD4+ cell fraction was increased (31%) by the treatment with TGF-beta in comparison to the cells not treated (25%), but the contents were decreased by suppressing the expression of snail gene with using the snail gene-specific siRNAs, regardless of the TGF-beta treatment (no treatment: from 25% to 17%, treated: from 31% to 20%). This indicates that the increase in the expression of FoxP3 in the CD4+ cells is due to the increased expression of snail gene in the Hs294T cells.

{3} Induction of FoxP3 Expression and Acquisition of Suppressive Activity of T Cell Proliferation in CD4+ Cell by Coculturing of Panc-1 Cell with F3 Cell or D10 Cell <Purpose>

By coculturing PBMCs with either F3 cells or D10 cells, it will be shown that an enhancement of expression of FoxP3 protein occurs in CD4+ cells among the PBMCs and that the CD4+ cells acquire an activity to suppress the proliferation of T cells.

<Experimental Method>

(1) Coculture of PBMCs with Tumor Cells (Panc-1 Cell or F3 Cell)

Panc-1 cells or F3 cells were cocultured with PBMCs in the same method as in {2} above.

(2) Coculture of CD4+ Cells with Fresh T Cells

The PBMCs having been cocultured with tumor cells for 3 to 5 days were overlaid on Ficoll (specific gravity of 1.090) and centrifuged (1500 rpm, 20 min, room temperature); a fraction of cells present in the interphase was separated and washed, then mixed with an magnetic bead-bound anti-CD4 antibody (MACS Antibody, Miltenyi Biotec) and incubated at 4° C. for 30 minutes; and CD4+ cells were isolated by using a MACS automated cell sorter (Miltenyi Biotec).

In the meantime, for observing proliferation responses of T cells, fresh PBMCs were obtained in the same method as in {2} above from the same healthy individual, and T cells (CD4+ cells or CD8+ cells) were isolated in the same method as above with using the MACS antibody (the anti-CD4 antibody or the anti-CD8 antibody). These fresh T cells ($2 \times 10^5$) were added with an anti-CD3 antibody (final concentration of 1 μg/mL) along with the CD4+ cells ($2 \times 10^5$) which were isolated from the PBMCs having been cultured with the tumor cells, and cultured in a 96-well plate for 4 days. After an addition of 1/10 volume of Premix WST-1 Solution (Takara Bio), the cells were further cultured for 24 hours. Then optical density (at 450-655 nm) was measured by a microplate reader and the measured values were taken as the amounts of proliferation of the T cells.

(3) Expression Analysis of FoxP3 Protein

The expression of FoxP3 protein was analyzed in the same method as in {2} above.

<Results>

(1) Expression Analysis of FoxP3 Protein

FIG. 2B shows the results of the FACS analyses.

Upper panels ("CD4+CD25+ in lymphocytes") show the results of the fractionation of cells according to expressions of CD4 and CD25, and the numbers in the panels indicate the contents (%) of CD4+CD25− cells (left) or CD4+CD25+ cells (right) in the lymphocyte fraction. Lower panels ("FoxP3+ in CD4+ fraction") show the expression levels of FoxP3+ protein in the CD4+ cell fractions (the expression level of FoxP3+ protein increases as the x-axis advances in each graph), and the numbers in the graphs indicate the contents (%) of FoxP3+ cells among the fraction of CD4+ cells present within the range where the expression was judged to be positive in comparison to the isotype control (rat IgG2a) for the anti-FoxP3 antibody used.

An enhancement of expression of FoxP3 was observed in the CD4+ cells by coculturing with the Panc-1 cells in which snail gene was not forced to be expressed ("Parent" in the figure: the expression level of FoxP3 was 30.83) in comparison to the cells without the coculturing with tumor cells ("No tumor" in the figure: 14.56). In contrast, further enhancement of the expression of FoxP3 was achieved by coculturing with the F3 cells where snail gene was forced to be expressed ("F3" in the figure: 43.44). These results indicate that there is a correlation between the expression level of snail gene and the expression enhancing capability for FoxP3.

Thus, the cells expressing snail gene can enhance the expression of FoxP3 protein in the cocultured CD4+ cells. The forced expression of snail gene to increase the expression level of Snail protein also increases the expression enhancing capability for FoxP3 protein.

It should be noted that because of the fact that the expression enhancing capability for FoxP3 was reduced when the expression of snail gene was suppressed by introducing the siRNAs specific for snail gene into the F3 cells, the expression enhancing capability for FoxP3 has been confirmed not to be an artifact due to variations among clones or the like, but indeed the consequence of the forced expression of snail gene.

(2) Coculture of CD4+ Cells with T Cells

Figure 2C:
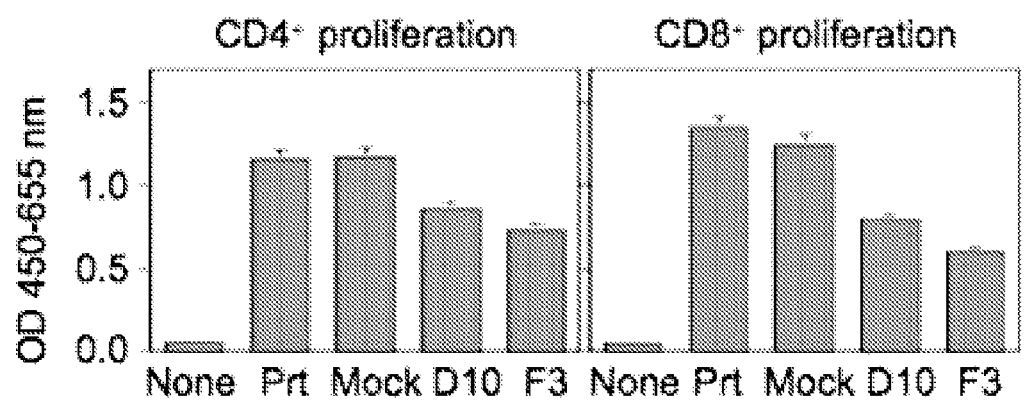
FIG. 2C shows suppression of proliferation of T cells by the CD4+ cells cocultured with Panc-1 cells, F3 cells or D10 cells in one example of the present invention.

FIG. 2C shows the results of the measurements for proliferation of respective T cells (CD4+ T cells in the left-hand panel, CD8+ T cells in the right-hand panel). "None" indicates a background value for the proliferation of T cells solely without addition of the anti-CD3 antibody or the CD4+ cells. As the positive controls, the proliferation was measured in the T cells to which only the anti-CD3 antibody was added but no CD4+ cells, and both CD4+ cells and CD8+ cells registered values greater than 2.0 (not shown).

While the proliferation of T cells was strongly suppressed by coculturing with Panc-1 cells (1 to 1.5 for "Prt" or "Mock" in the figure), the proliferation was even further suppressed when the T cells were cocultured with D10 cells or F3 cells, showing their significant suppressive effect (P<0.001).

Thus, the cells expressing snail gene are capable of allowing the cocultured CD4+ cells to acquire the proliferation suppressing capability against T cells, i.e., capable of inducing differentiation into regulatory T cells.

{4} Induction of Expression of FoxP3 in CD4+ Cells by Coculturing with HCT116 Cells <Purpose>

An experiment according to {1} and {2} above was conducted with using HCT116 cells, a human intestinal cancer cell line, in place of the Panc-1 cells. The experimental methods were the same as those in {1} and {2} above.

<Results>

Figure 3:
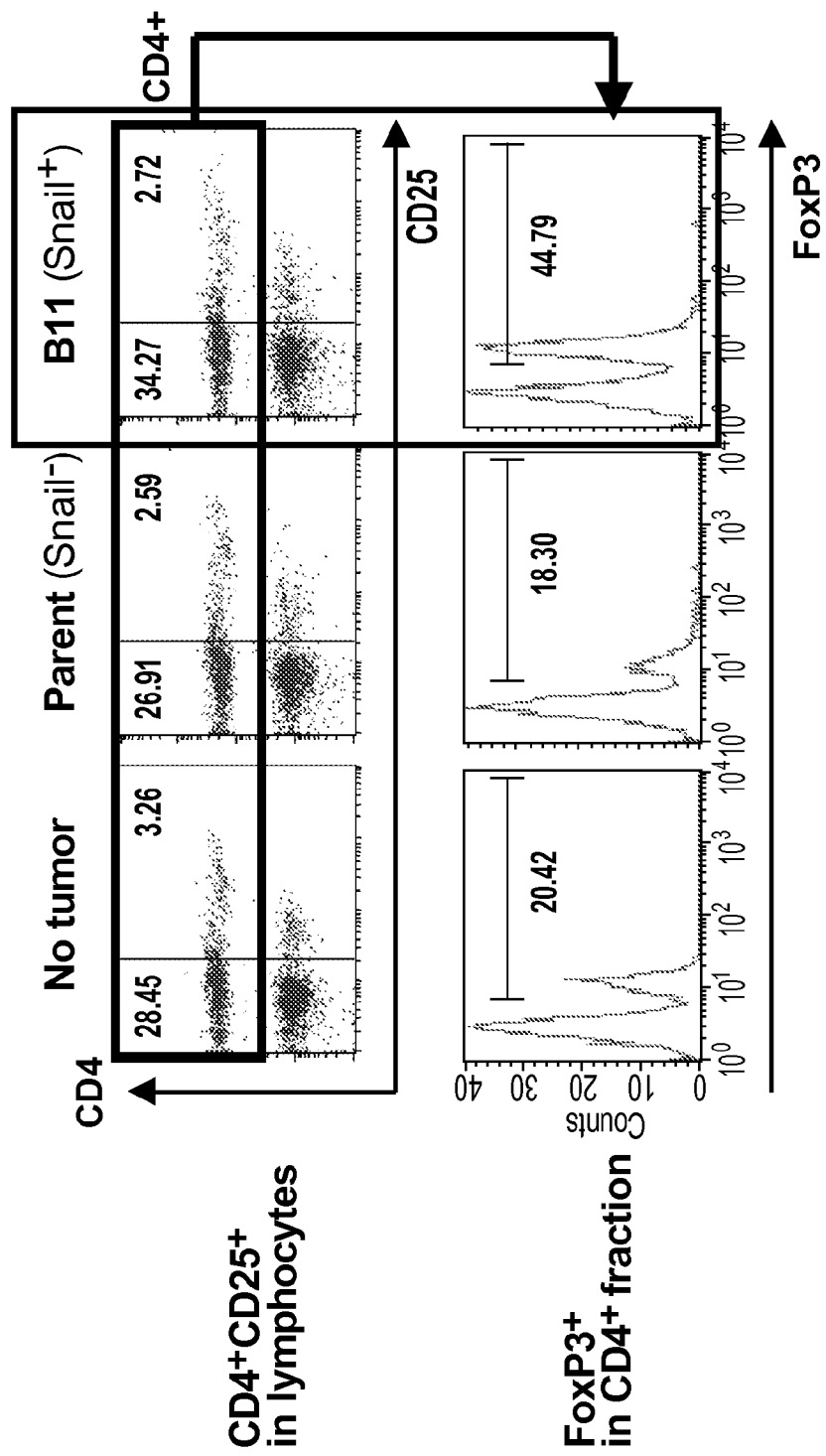
FIG. 3 shows an induction of expression of FoxP3 in CD4+ cells by coculturing PBMCs with HCT116 cells in one example of the present invention.

FIG. 3 shows the results of the FACS analyses.

The expression of FoxP3 was not enhanced by coculturing with the HCT116 cells in which Snail was not forced to be expressed ("Parent" in the figure: the expression level of FoxP3 was 18.30) in comparison to the cells without the coculturing with tumor cells ("No tumor" in the figure: 20.42). In contrast, the expression of FoxP3 was enhanced by coculturing with the B11 Clone where snail gene was forced to be expressed ("B11" in the figure: 44.79). Thus, a correlation between the expression level of snail gene and the expression enhancing capability for FoxP3 was observed in multiple cancer types.

{5} Induction of Expression of FoxP3 in CD4+ Cells by Cell Culture Supernatant from Clone with Forced Expression of Snail Gene <Purpose>

It will be shown that not only the F3 cell by itself but also a cell culture supernatant from the F3 cell enhances the expression of FoxP3 protein in CD4+ cells.

<Methods>

(1) Method for Preparing Culture Supernatant $1\times10^5$ of tumor cells were cultured in a 25 cm² flask for 3 to 4 days, and then a supernatant from the culture was transferred to a test tube and centrifuged (3000 rpm, 20 min, 4° C.), from which a supernatant was taken as the culture supernatant, and stored at 4° C. until used in the following experiment.

(2) Method for Treatment by Culture Supernatant

A suspension of $5\times10^5$ of PBMCs (or a fraction thereof) was mixed with an equal volume of the culture supernatant from the tumor cells in a 24-well plate and cultured therein, i.e., in the 2-fold diluted culture supernatant from the tumor cells, at 37° C. and 5% $CO_2$ for 3 to 4 days. Afterwards, the PBMCs were recovered. As for the negative control, a similar experiment was conducted with using a medium which was not used for a culture, in place of the culture supernatant from the tumor cells.

(3) Others

The expression analysis of FoxP3 protein was conducted according to {2} above.

<Results>

Figure 4A:
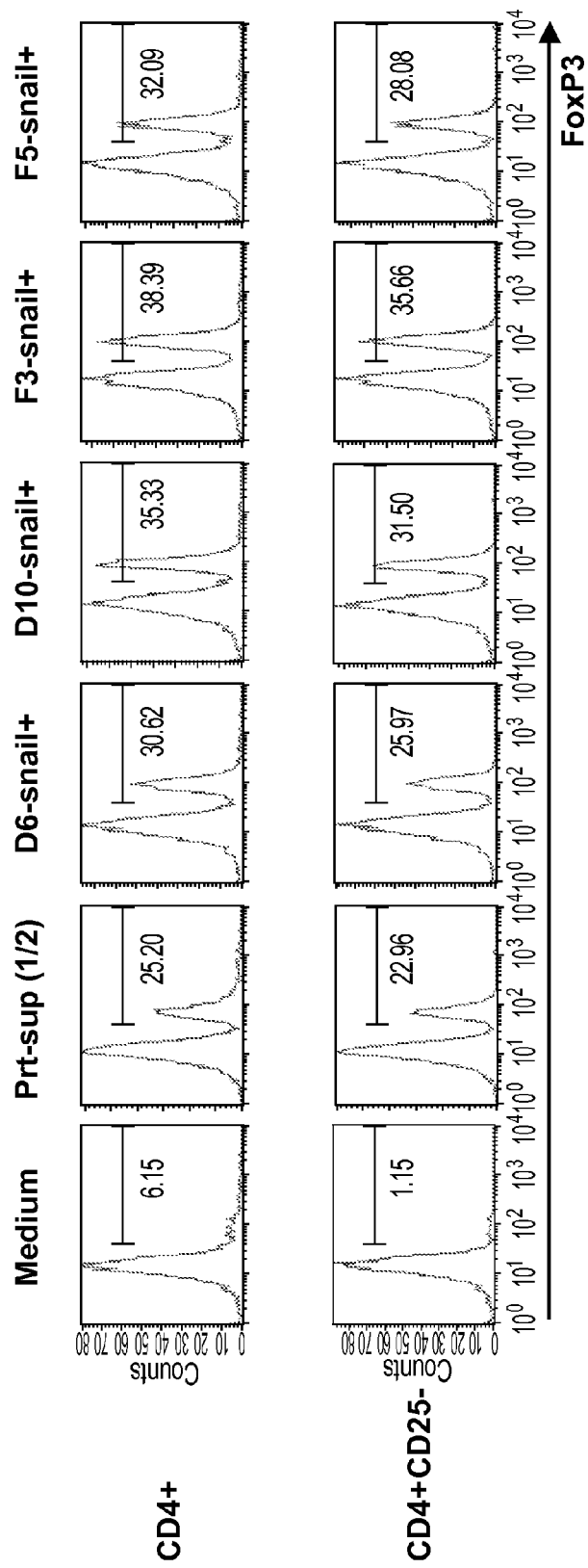
FIGS. 4A and 4B show the induction of expression of FoxP3 in CD4+ cells by culture supernatants from the cell clones where snail gene was forced to be expressed in one example of the present invention.
Figure 4B:
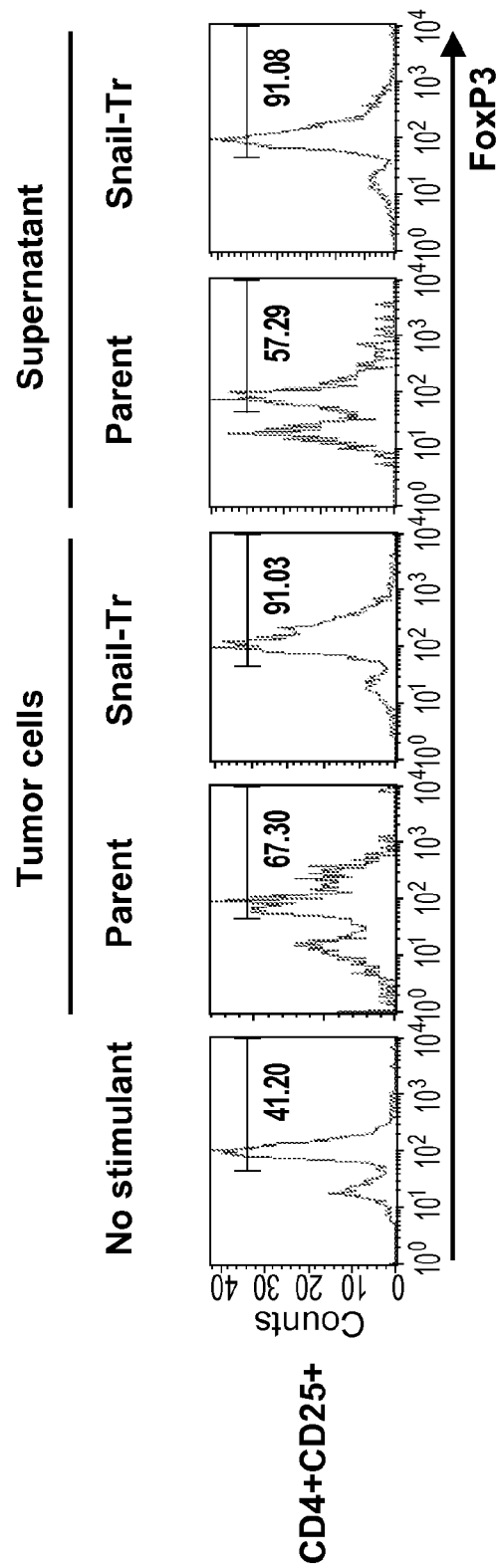

FIG. 4 shows the results of the FACS analyses.

The culture supernatant from the parent cell line ("Prt-sup" in panel A, "Parent" in panel B) as well as the Snail-introduced cells ("D6-snail+", "D10-snail+", "F3-snail+", and "F5-snail+" in panel A, "Snail-Tr" in panel B) enhanced the expression of FoxP3 protein in each of CD4+ cells (panel A, top row), CD4+ CD25− cells (panel A, bottom row), and CD4+CD25+ cells (Panel B), in comparison to the cases where only the culture medium was used ("Medium" in panel A, "No stimulant" in panel B). This indicates that the enhancing action for the expression of FoxP3 protein by the expression of Snail protein is mediated by a humoral factor.

Thus, the culture supernatant from the cells expressing Snail protein can be also used as an enhancer for the expression of FoxP3 protein.

It should be noted that since the CD4+CD25+ cells are at an advanced stage in the course of differentiation into regulatory T cells, in some cases FoxP3 protein are being expressed at the maximum level, and thus the effect of the supernatant from the Snail-expressing cells might not be observed (see FIG. 6 below).

{6} Genes Whose Expression Increases by Forced Expression of Snail Protein in Panc-1, HCT116 and Hs294T Cell Lines <Purpose>

It will be shown that the expression of MCP1, TSP1, FSTL1 and secretory IL-13Ra2 increases by the forced expression of Snail protein in Panc-1, HCT116 and Hs294T.

<Methods>

(1) Method for Measuring Expression Level of MCP1, TSP1, FSTL1 or IL-13Ra2

Commercially available ELISA kits were used to detect the protein expression of each of MCP1 (by ELISA kit #EHMCP1 from ENDOGEN), TSP1 (by ELISA kit #CYT168 from CHEMICON) and secretory IL-13Ra2 (by ELISA kit #ab46112 from ABCAM) with following their attached protocols. As for the negative control, a similar experiment was conducted with using a medium which was not used for a culture.

Meanwhile, the gene expression of FSTL1 was measured by the RT-PCR method as described in {1} above. The following oligonucleotides were used as the primers. As for the negative control (NC), a similar experiment was conducted without addition of an mRNA.

```
                                          (SEQ ID NO: 11)
        Forward2    5'-GCACAGGCAACTGTGAGAAA-3'

(SEQ ID NO: 12)
        Reverse2    5'-CATAGTGTCCAAGGGCTGGT-3'
```

(2) Method for Detecting Intracellular Localization of IL-13Ra2 Protein

The expression of the membrane-bound form of IL-13Ra2 as well as those present in cytoplasm/nuclei of tumor cells were detected similarly to the method for the expression of Snail protein, by the immunostaining as described in {1}(3) above.

<Results>

Figure 5A:
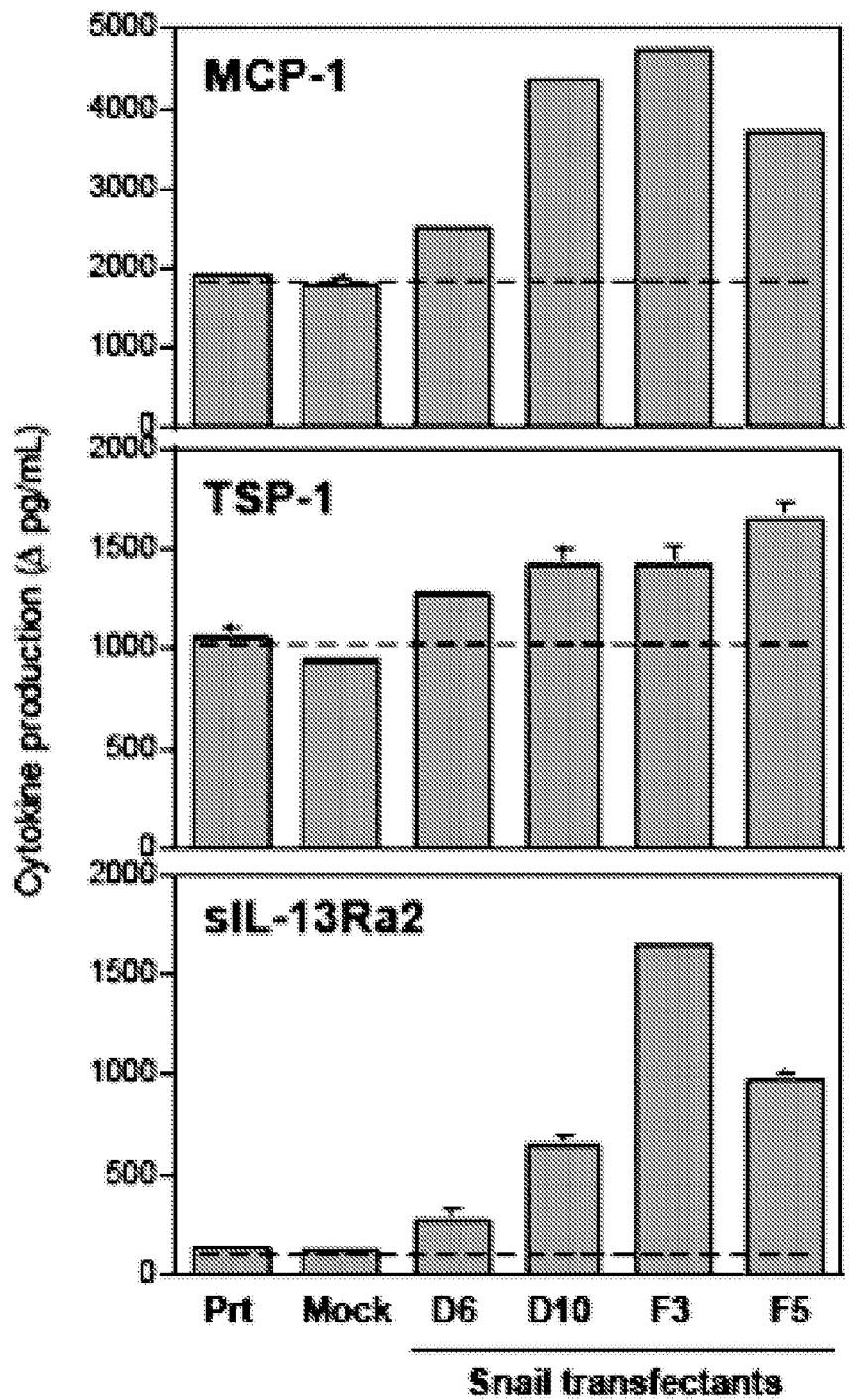
FIGS. 5A-5C show the genes whose expression was increased by forced expression of Snail protein in each of Panc-1, HCT116 and Hs294T cell lines in one example of the present invention.
Figure 5B:
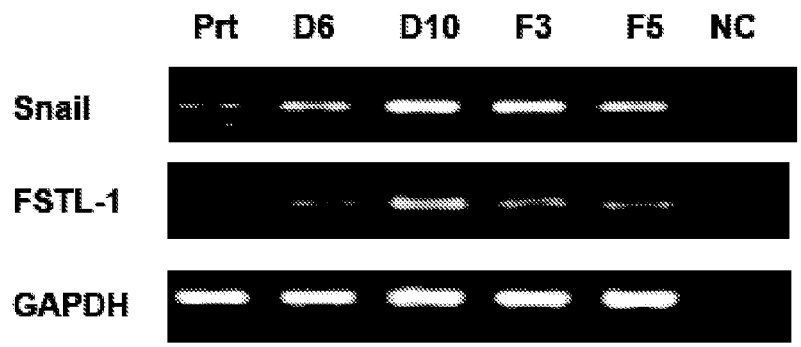

The results are shown in FIG. 5. (A) shows the results of comparisons of protein expression levels of MCP1, TSP1 and sIL-13Ra2 (secretory form), and (B) shows the results of a comparison of mRNA expression levels of FSTL-1. (C) shows the localization of IL-13Ra2 in respective types of tumor cells.

Figure 5C:
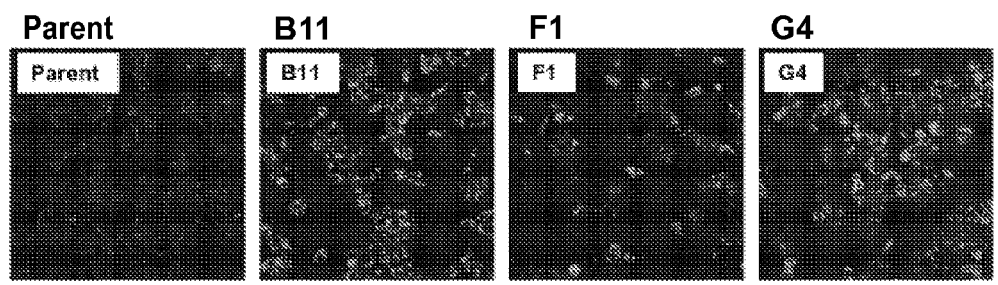

In each of Snail-expressing clones (D6, D10, F3 and F5), the expression of the abovementioned cytokines were increased in comparison to the parent cell line (Prt). The increase in the expression of IL-13Ra2 was observed not only for its secretory form (FIG. 5A) but also those on the membrane as well as in the cytoplasm and nuclei of each clone as shown in FIG. 5C.

Thus, an enhancement of the activity of Snail protein can enhance the expression of MCP1, TSP1, IL-13Ra2 and FSTL-1.

{7} Suppression of Enhancement of FoxP3 Protein Expression by F3 Clone Using Antibodies to Each of MCP1, TSP1, FSTL1 and IL13Ra2 Proteins <Purpose>

It will be shown that antibodies to each of MCP1, TSP1, FSTL1 and IL13Ra2 proteins inhibit the action of F3 clone to enhance the expression of FoxP3 protein.

<Methods>

(1) Antibodies Used in this Example

Commercially available products of an anti-MCP1 antibody (BD PharMingen #551226), an anti-TSP1 antibody (ABCAM #ab3131), an anti-FSTL1 antibody (R&D #MAB1694), an anti-TGF-beta1 antibody (R&D #MAB246), an anti-IL-10 antibody (R&D #MAB2171), an anti-IL-13Ra2 antibody (R&D #AF146) and a mouse IgG antibody (BD Pharmingen #557273) were used.

(2) Recovery of Culture Supernatants Added with Antibodies

The anti-MCP1 antibody, the anti-TSP1 antibody, the anti-FSTL1 antibody or the anti-IL13Ra2 antibody was added at a final concentration of 1 to 5 μg/mL either directly to inactivated tumor cells or into their culture medium, then the cells were cocultured with PBMCs for 3 days, and the PBMCs were recovered. The anti-TGF-beta1 antibody and the anti-IL-10 antibody were used as the positive control, and the mouse IgG was used as the negative control.

(3) Others

Preparation of the culture supernatant from tumor cells and the expression analysis of FoxP3 protein were conducted according to {5} above.

<Results>

Figure 6:
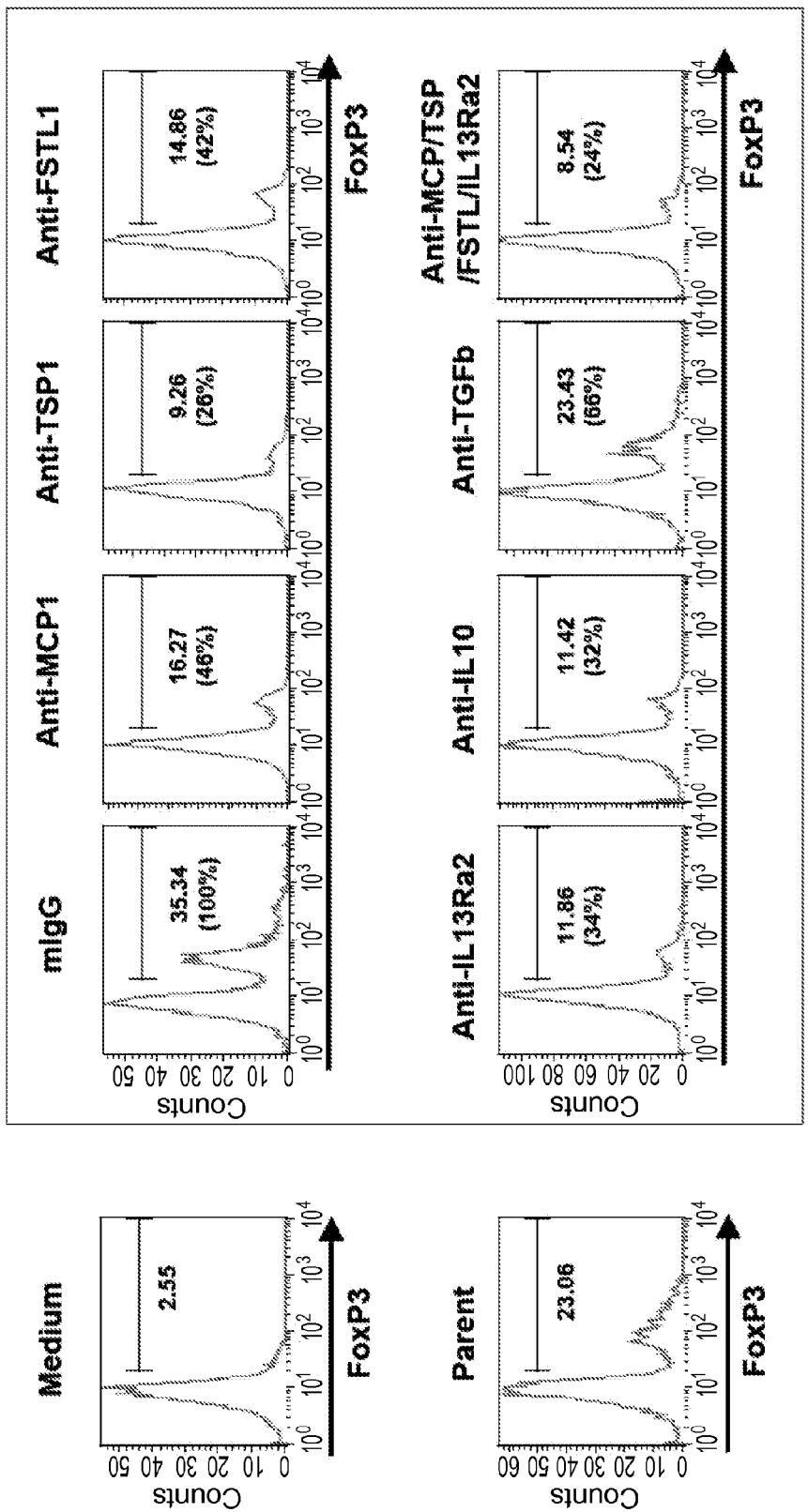
FIG. 6 shows suppression of enhancement of FoxP3 protein expression in CD4+ cells by F3 clone using an anti-MCP1 antibody, an anti-TSP1 antibody, an anti-FSTL1 antibody or an anti-IL-13Ra2 antibody in one example of the present invention.
Figure 7A:
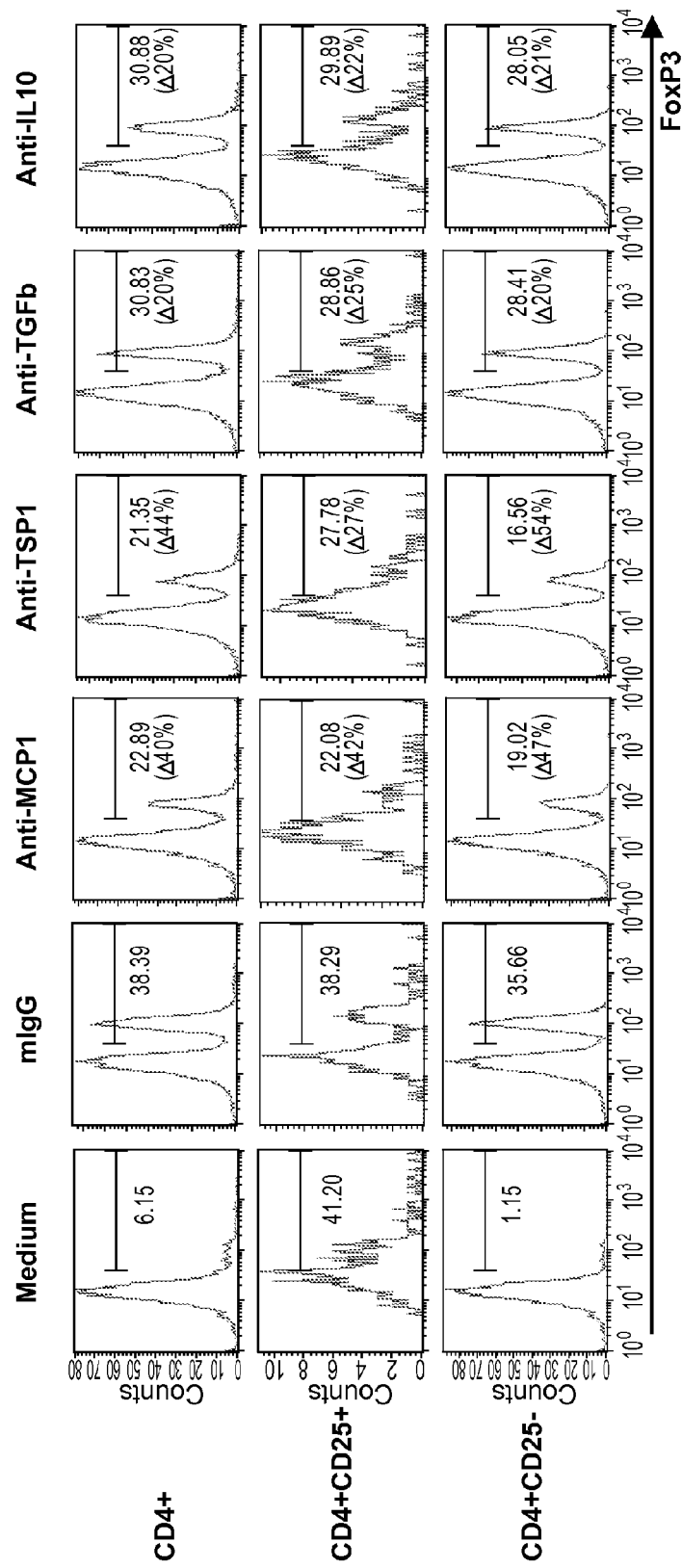
FIG. 7A shows suppression of enhancement of FoxP3 protein expression in CD4+ cells, CD4+CD25+ cells and CD4+ CD25− cells by F3 clone using the anti-MCP1 antibody or the anti-TSP1 antibody in one example of the present invention.
Figure 7B:
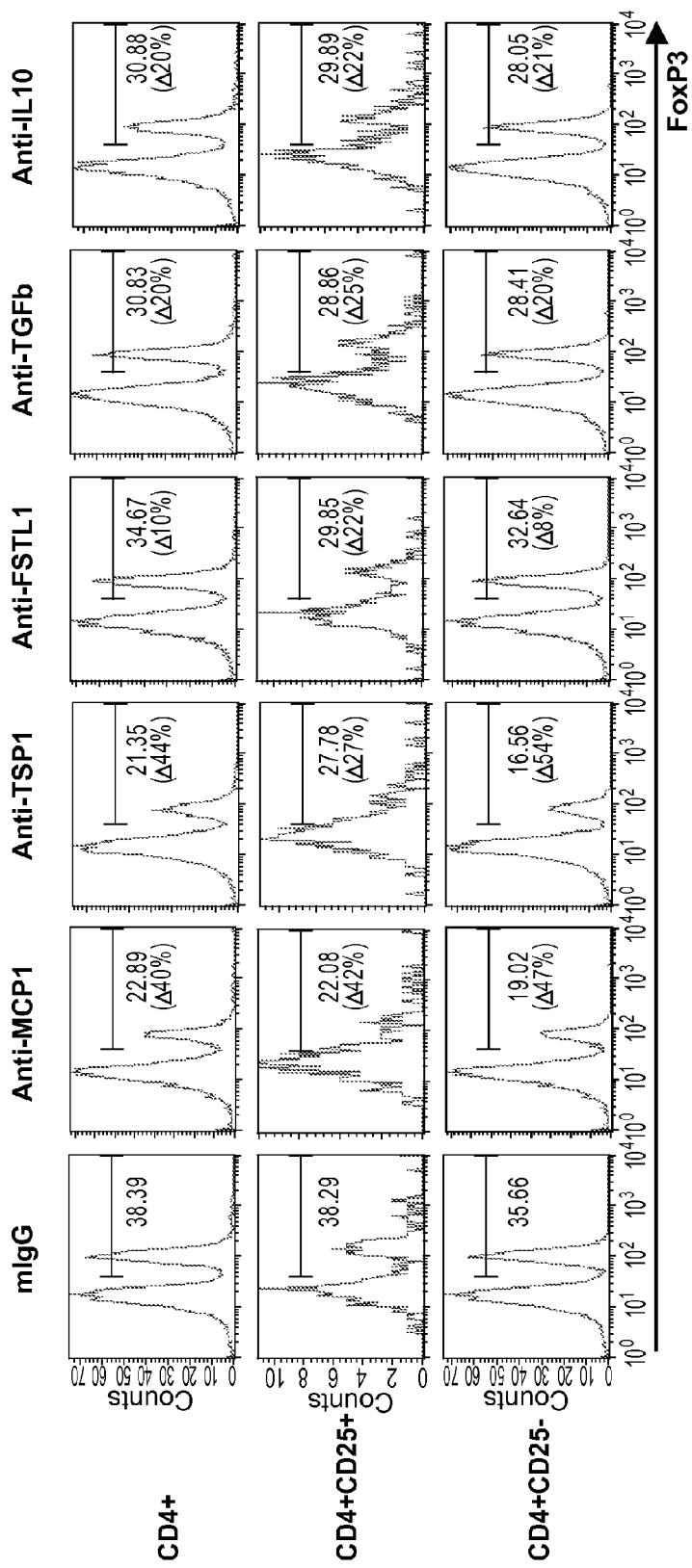
FIG. 7B shows suppression of enhancement of FoxP3 protein expression in CD4+ cells, CD4+CD25+ cells and CD4+ CD25− cells by F3 clone using the anti-FSTL1 antibody in one example of the present invention.

FIG. 6 shows the results of the measurements for the expression levels of FoxP3 protein in the CD4+ cells with which the respective antibodies were used. FIG. 7 shows the results of measurements for the expression levels of FoxP3 protein in the CD4+ cells, CD4+CD25+ cells and CD4+CD25− cells with which the respective antibodies were used.

TGF-b and IL-10 are known to be involved in the induction of expression of FoxP3 protein, and the anti-TGF-b antibody and the anti-IL-10 antibody were indeed capable of suppressing the expression enhancing capability for FoxP3 protein of the culture supernatant of F3 clone in each of CD4+ cells, CD4+CD25+ cells and CD4+CD25− cells. For example, the administration of the anti-TGF-b antibody ("Anti-TGF-b" in the figures) reduced the expression levels of FoxP3 protein from 35.34 to 23.43 (FIG. 6) or from 38.39 to 30.63 (FIG. 7) in CD4+ cells, from 38.39 to 28.86 in CD4+CD25+ cells, and from 35.66 to 28.41 in CD4+CD25− cells. Similarly, the anti-IL-10 antibody ("Anti-IL-10" in the figures) reduced the expression levels of FoxP3 protein to 11.42 (FIG. 6) or to 30.88 (FIG. 7) (in CD4+ cells), to 29.89 (in CD4+CD25+ cells) and to 28.05 (in CD4+CD25− cells).

Meanwhile, the administration of the anti-MCP1 antibody ("Anti-MCP1" in the figures) also reduced the expression levels of FoxP3 protein to 16.27 (FIG. 6) or to 22.89 (FIG. 7) (in CD4+ cells), to 22.08 (in CD4+CD25+ cells) and to 19.02 (CD4+CD25− cells), and the anti-TSP1 antibody ("Anti-TSP1" in the figures) similarly reduced the expression levels of FoxP3 protein to 9.26 (FIG. 6) or to 21.35 (FIG. 7) (in CD4+ cells), to 27.78 (in CD4+CD25+ cells) and to 16.56 (in CD4+CD25− cells). The administration of the anti-FSTL1 antibody ("Anti-FSTL1" in the figures) showed smaller effect, but still it reduced the expression levels of FoxP3 protein to 14.86 (FIG. 6) or to 34.67 (FIG. 7) (in CD4+ cells), to 29.85 (in CD4+CD25+ cells) and to 32.64 (in CD4+CD25− cells). The administration of the anti-IL13Ra2 antibody ("Anti-IL13Ra2" in the figure) reduced the expression level from 35.34 to 11.86 (FIG. 6) (in CD4+ cells). Thus, the anti-MCP1 antibody, the anti-TSP1 antibody, the anti-FSTL1 antibody and the anti-IL13Ra2 antibody are shown to be capable of suppressing the expression enhancing capability for FoxP3 protein of the culture supernatant.

When the anti-MCP1 antibody, the anti-TSP1 antibody, the anti-FSTL1 antibody and the anti-IL13Ra2 antibody were used together, a maximum effect of suppression of expression enhancing capability for Fox3 protein was observed in CD4+ cells (reduction from 35.34 to 8.54) (FIG. 6), indicating that each of these cytokines redundantly contributes to the enhancing action for the expression of FoxP3 protein by the culture supernatant of F3 clone.

Therefore, a substance that inhibits function of MCP1, TSP1 or an FSTL1 can inhibit the expression enhancing capability for FoxP3 protein of the Snail-expressing cells.

{8} Suppression for Enhancement of Expression of FoxP3 Protein Using Anti-IL-13Ra2 Antibody <Purpose>

It will be shown that anti-IL-13Ra2 antibody inhibits the activity of B11 clone to enhance the expression of FoxP3 protein.

<Methods>

An experiment according to {7} above was conducted except that the anti-MCP1 antibody and the anti-IL-13Ra2 antibody were used as the antibodies and that B11 clone was used as the tumor cells. As for the positive control to inhibit the activity to enhance the expression of FoxP3, an anti-IL-13 antibody was used in this case.

<Results>

Figure 8:
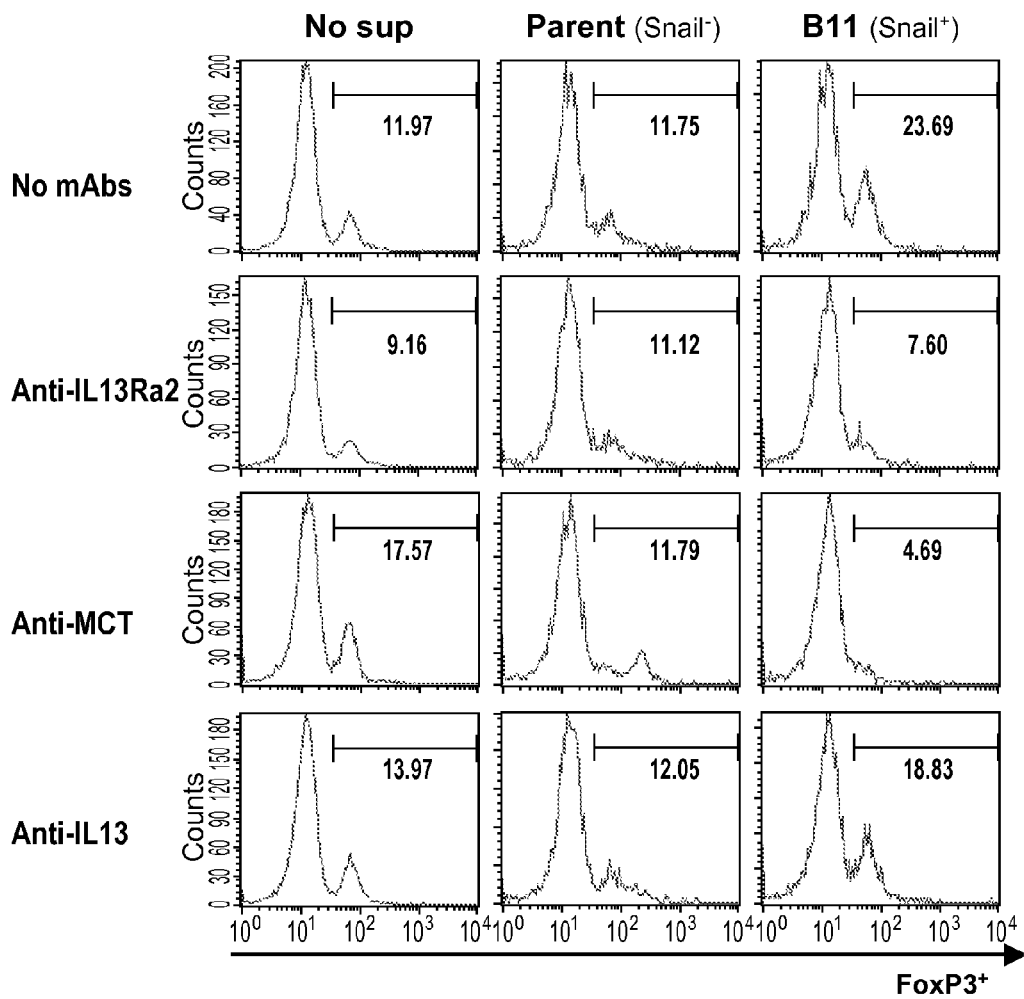
FIG. 8 shows suppression of enhancement of FoxP3 protein expression using the anti-IL-13Ra2 antibody in one example of the present invention.

FIG. 8 shows the results with using the anti-MCP1 antibody and the anti-IL-13Ra2 antibody.

The anti-MCP1 antibody reduced the expression of FoxP3 protein which had been enhanced by the culture supernatant of B11 clone from 23.69 (no antibody; "No mAbs" in the figure) to 4.69 (with antibody administration; "Anti-MCT" in the figure), and the anti-IL-13Ra2 antibody reduced the expression to 7.60 (with antibody administration; "Anti-IL13Ra2" in the figure). Thus, these antibodies can inhibit the activity for enhancement of FoxP3 protein expression by the culture supernatant of B11 clone. It should be noted that the effect by the anti-IL-13Ra2 antibody was not observed in the case of the parent cell of HCT116 because the HCT116 cells do not express Snail.

Thus, a substance that inhibits function of not only MCP1 but also IL-13Ra2 can inhibit the expression enhancing capability for FoxP3 protein of Snail-expressing cells.

{9} Suppression of Enhancement of Expression of Foxp3 Protein by Mouse Melanoma B16-F10 Using Anti-MCP1 Antibody and Anti-IL-13Ra2 Antibody <Purpose>

It will be shown that the anti-MCP1 antibody and the anti-IL-13Ra2 antibody inhibit the activity for enhancement of the FoxP3 protein expression in mouse melanoma B16-F10.

<Methods>

(1) Method for Preparing Mouse Spleen Cell

Mouse spleen cells were used as the immune cell in place of the bulk PBMCs. First, a spleen was removed from a mouse and homogenized, then the cell suspension was separated by using Ficoll similarly to the case of human bulk PBMCs, and a fraction of cells present in the interphase was used.

(2) Others

The experiment was conducted basically in the same method as the case of human cultured cells, but the coculturing or the culturing in the presence of culture supernatant was conducted for 5 to 6 days in the case of the mouse melanoma, in contrast to 3 to 4 days in the case of the human cells.

<Results>

Figure 9:
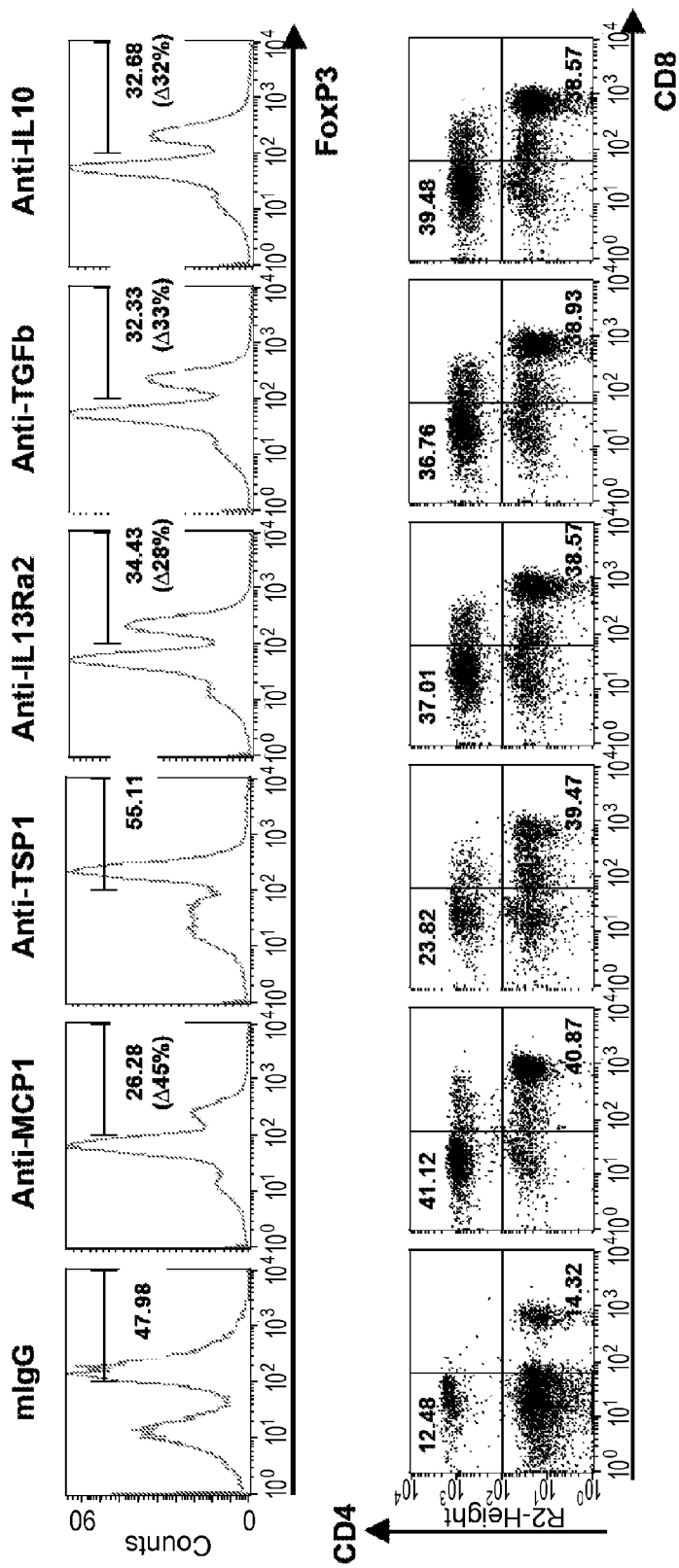
FIG. 9 shows suppression of enhancement of FoxP3 protein expression in mouse melanoma B16-F10 using the anti-MCP1 antibody or the anti-IL-13Ra2 antibody in one example of the present invention.

FIG. 9 (upper panels) shows the results with using the anti-MCP1 antibody, the anti-TSP1 antibody and the anti-IL-13Ra2 antibody. The mouse IgG was used as the negative control, and the anti-TGF-b antibody and the anti-IL-10 antibody were used as the positive control.

The anti-TSP1 antibody did not suppress the enhancing action on the FoxP3 protein expression in mouse melanoma B16-F10, but the anti-MCP1 antibody and the anti-IL-13Ra2 antibody suppressed the enhancing action on the FoxP3 protein expression by about 28 to 45% as shown in the figure.

Thus, the effect of suppression of the enhancement of FoxP3 protein expression can be observed not only in human tumor cells but also in mouse tumor cells.

{10} Enhancing Action of Cytokines MCP1, TSP1, FSTL1 and Secretory IL-13Ra2 on the FoxP3 Protein Expression <Purpose>

It will be shown that each of the cytokines MCP1, TSP1, FSTL1 and secretory IL-13Ra2 enhances the expression of FoxP3 protein in CD4+ cells.

<Methods>

An experiment according to {5} above was conducted except that a medium supplemented with either of the cytokines at 1 ng/mL was used in place of the culture supernatant. As the positive control, culture supernatants from Panc-1 cell and F3 clone as well as the cytokines TGF-b and IL-10 were used. As for the each cytokine, the following commercially available products were used: MCP1: R&D, #279-MC; TSP1: R&D #3074-TH; FSTL1: R&D #669-FO; secretory IL-13Ra2: Abcam #ab46112; TGF-b: R&D #100-B; and IL-10: eBioscience #34-8109.

<Results>

Figure 10:
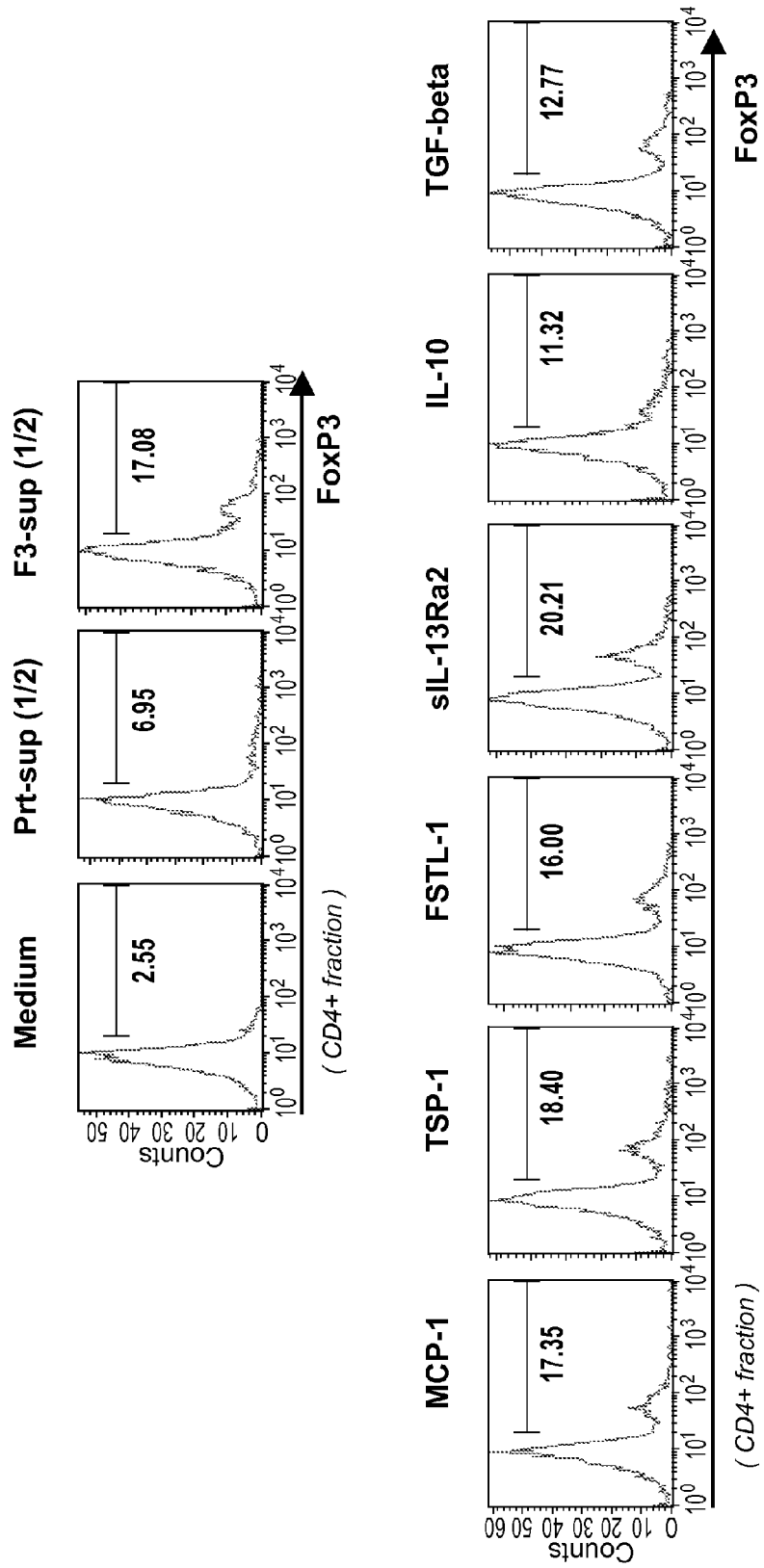
FIG. 10 shows the action of MCP1, TSP1, FSTL1 and secretory IL-13Ra2 to enhance the expression of FoxP3 protein in one example of the present invention.

FIG. 10 shows the results of the measurements for the expression of FoxP3 protein.

In comparison to the case where the medium without the addition of a cytokine was used (designated as "Medium" in the figure; the expression level was 2.55), enhancing actions on the expression of FoxP3 protein, similar to that of the culture supernatant from F3 clone (the expression level was 17.08), were observed by the addition of each of MCP1 protein (the expression level was 17.35), TSP1 protein (the expression level was 18.40), FSTL1 protein (the expression level was 16.00) and secretory IL-13Ra2 protein (the expression level was 20.21).

Thus, each of the cytokines MCP1, TSP1, FSTL1 and secretory IL-13Ra2 is useful as an agent for enhancing the expression of FoxP3 protein.

{11} Direct and Indirect Actions of Snail-Expressing Cell on Enhancement of the FoxP3 Protein Expression <Purpose>

It will be shown that there are direct and indirect actions of Snail-expressing cells on enhancement of the FoxP3 protein expression, and that the indirect action involves at least a dendritic cell.

<Methods>

By using isolated CD4+ cells as the immune cell in place of the bulk PBMCs, the expression level of FoxP3 protein in the CD4+ cells was examined in each of the following cases: (1) F3 cells were added to CD4+ cells only; (2) F3 cells were added to CD4+ cells plus dendritic cells (DCs); (3) F3 cells were added to CD4+ cells plus other cells (other cells, "others", are remaining cells after removal of CD4+ cells and dendritic cells from bulk PBMCs); (4) culture supernatant of F3 cells was added to CD4+ cells only; (5) coculture supernatant of F3 cells/DCs was added to CD4+ cells only; (6) coculture supernatant of F3 cells/others was added to CD4+ cells only; and (7) coculture supernatant of F3 cells/DCs/others was added to CD4+ cells only.

The CD4+ cells and CD11c+ cells (dendritic cells) were isolated from the bulk PBMCs by using MACS Antibodies (Miltenyi Biotec) in the same method as in (2) above. Other experimental methods were also the same as above.

<Results>

Figure 11:
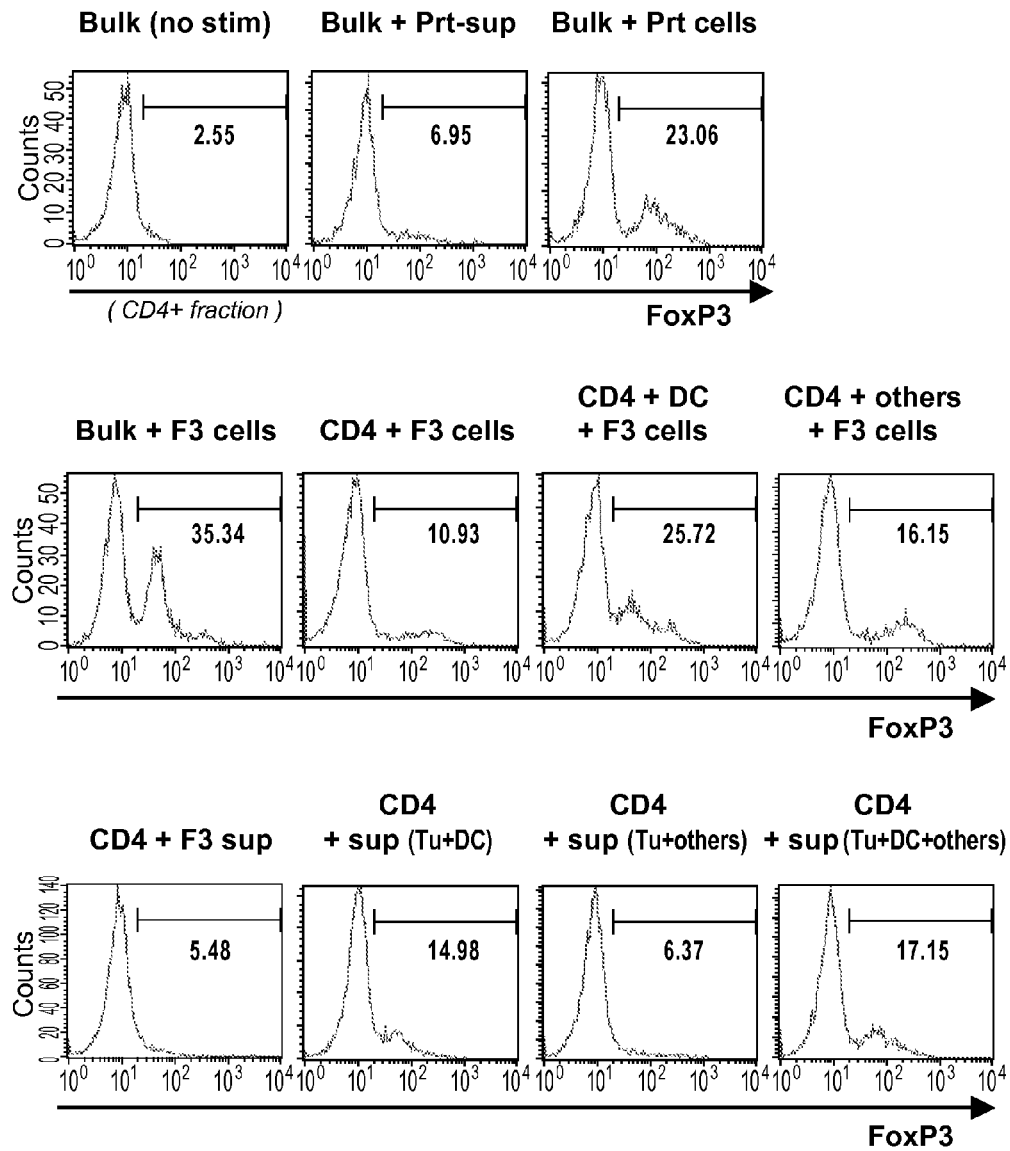
FIG. 11 shows a direct action and an indirect action of Snail-expressing cells to enhance the expression of FoxP3 protein in one example of the present invention.

FIG. 11 shows the results of the measurements for the expression of FoxP3 protein. The panels in the middle of the figure show the results of experiments where the cells were added, and those at the bottom show the results of experiments where the culture supernatants were added.

The addition of Bulk PBMCs instead of CD4+ cells only to F3 cells decreased the expression level of FoxP3 protein (from 35.34 in "Bulk+F3 cells" to 10.93 in "CD4+F3 cells"). When DCs or others were further added, the expression level of FoxP3 protein was increased (to 25.72 in "CD4+DC+F3 cells" or 16.15 in "CD4+others+F3 cells"), indicating that the increase in the expression level of FoxP3 protein in CD4+ cells among the bulk PBMCs involves cells other than the CD4+ cells (DCs or cells other than DCs).

Meanwhile, when F3 cells were added to CD4+ cells only, the expression level of FoxP3 protein was increased (to 10.93 in "CD4+ F3") in comparison to the case where the bulk PBMCs was not stimulated (2.55 in "Bulk (no stim)"), indicating that there is also a mechanism where the F3 cell by itself or a humoral factor in its culture supernatant acts directly on the CD4+ cell.

In all the cases where the cells were added, the expression levels of FoxP3 protein were about twice as high as the cases where the corresponding cell culture supernatants were added. For example, "CD4+F3 cells" yielded 10.93, whereas "CD4+F3sup" yielded 5.48; "CD4+DC+F3 cells" yielded 25.72, whereas "CD4+sup (Tu+DC)" yielded 14.9; and "CD4+others+F3 cells" yielded 16.15, whereas "CD4+sup (Tu+others)" yielded 6.37. Therefore, it is considered that not only the action via a humoral factor but also the direct intercellular interaction contributes to the enhancement of expression of FoxP3 protein.

Figure 12:
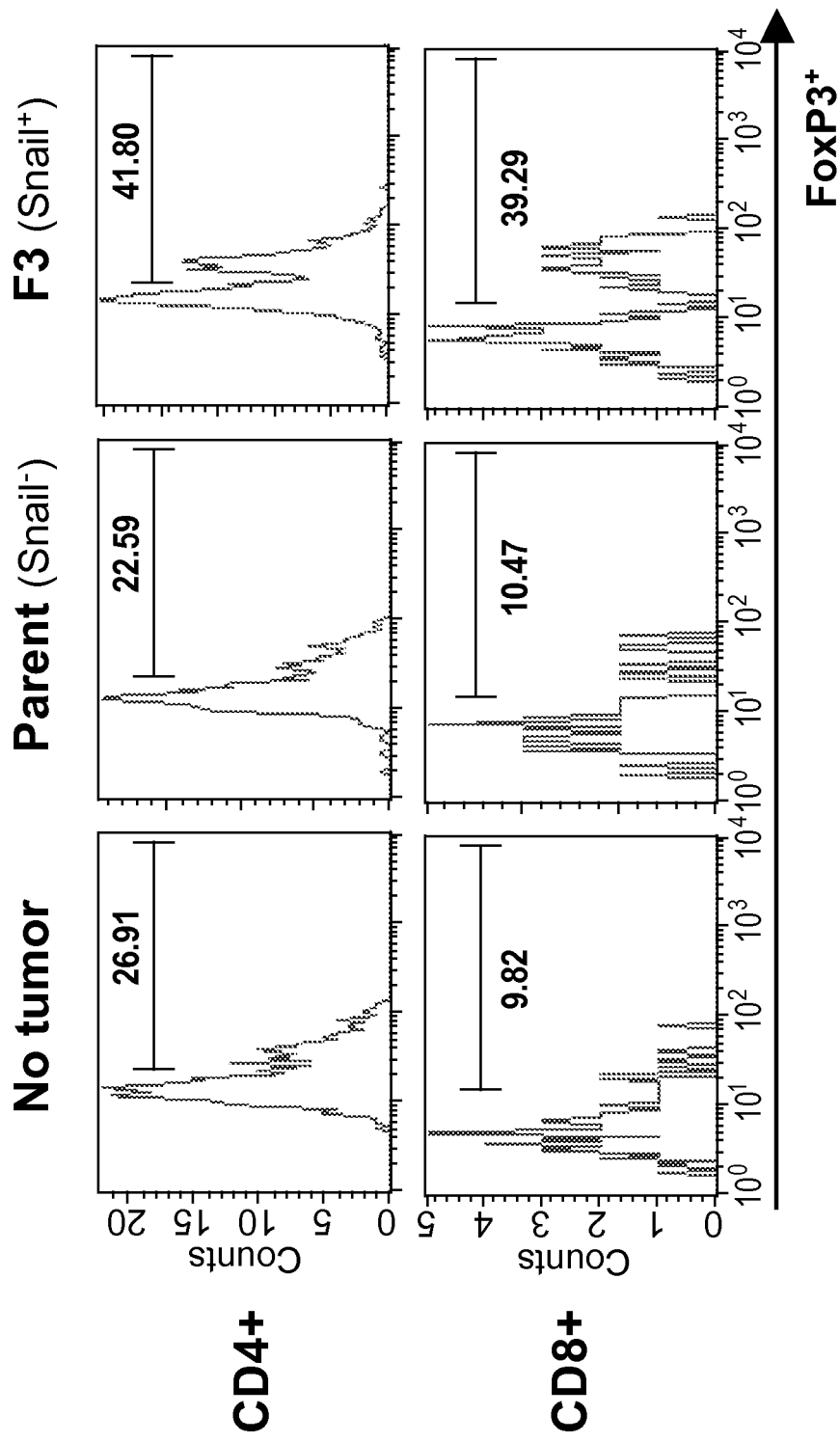
FIG. 12 shows induction of the FoxP3 expression in CD8+ cells by a culture supernatant of a cell clone in which snail gene is forced to be expressed in one example of the present invention.

{12} Induction of Expression of FoxP3 in CD8+ Cell by Culture Supernatant of Cell Clone with Forced Expression of Snail Gene <Purpose>
It will be shown that similarly to the case where CD4+ cells are used, a cell culture supernatant of Clone F3 in which snail gene is forced to be expressed also induces the expression of FoxP3 protein in CD8+ cells.
<Methods>
An experiment was conducted in the same method as in {5} above except that CD8+ cells were used as the cells to be treated in place of the CD4+ cells.
<Results>
FIG. 12 shows the results of the measurements for the expression of FoxP3 protein.

Similarly to the results obtained by using CD4+ cells, the cell culture supernatant from the parent cell line Panc-1 ("Parent(Snail-)" in the figure) increased the expression of FoxP3 protein only slightly in comparison to the case where no supernatant from tumor cells was added ("No Tumor" in the figure), whereas an enhanced expression of FoxP3 protein was observed in CD8+ cells by the addition of the cell culture supernatant from F3 ("F3(Snail+)" in the figure).

Thus, a culture supernatant of Snail-expressing cells can also enhance the expression of FoxP3 protein in CD8+ cells.

{13} Suppression of Enhancement of FoxP3 Protein Expression in CD8+ Cell Using Anti-TSP1 Antibody and Anti-IL-13Ra2 Antibody <Purpose>
It will be shown that similarly to the case where CD4+ cells are used, the anti-TSP1 antibody and the anti-IL-13Ra2 antibody also suppress the enhancement of expression of FoxP3 protein in CD8+ cells.
<Methods>
An experiment was conducted in the same method as in {7} above except that CD8+ cells were used as the cells to be treated in place of the CD4+ cells. The anti-MCP1 antibody or the anti-TSP1 antibody was used for F3 cells, and the anti-IL-13Ra2 antibody was used for B11 cells. As for the negative control, the same experiment was conducted with using the mouse IgG antibody.
<Results>
FIG. 13 shows the results of the measurements for the expression of FoxP3 protein where the anti-MCP1 antibody and the anti-TSP1 antibody were used for F3 cells, and FIG. 14 shows the results where the anti-IL-13Ra2 antibody was used for B11 cells.

Figure 13:
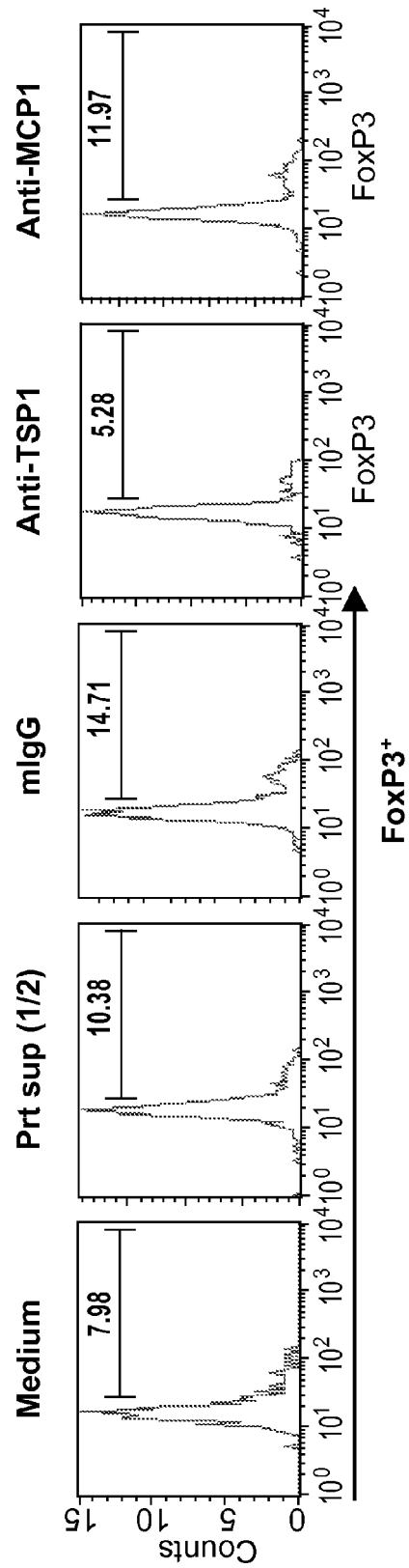
FIG. 13 shows suppression of the action of F3 cells to enhance the expression of FoxP3 protein in CD8+ cells using the anti-MCP1 antibody or the anti-TSP1 antibody in one example of the present invention.
Figure 14:
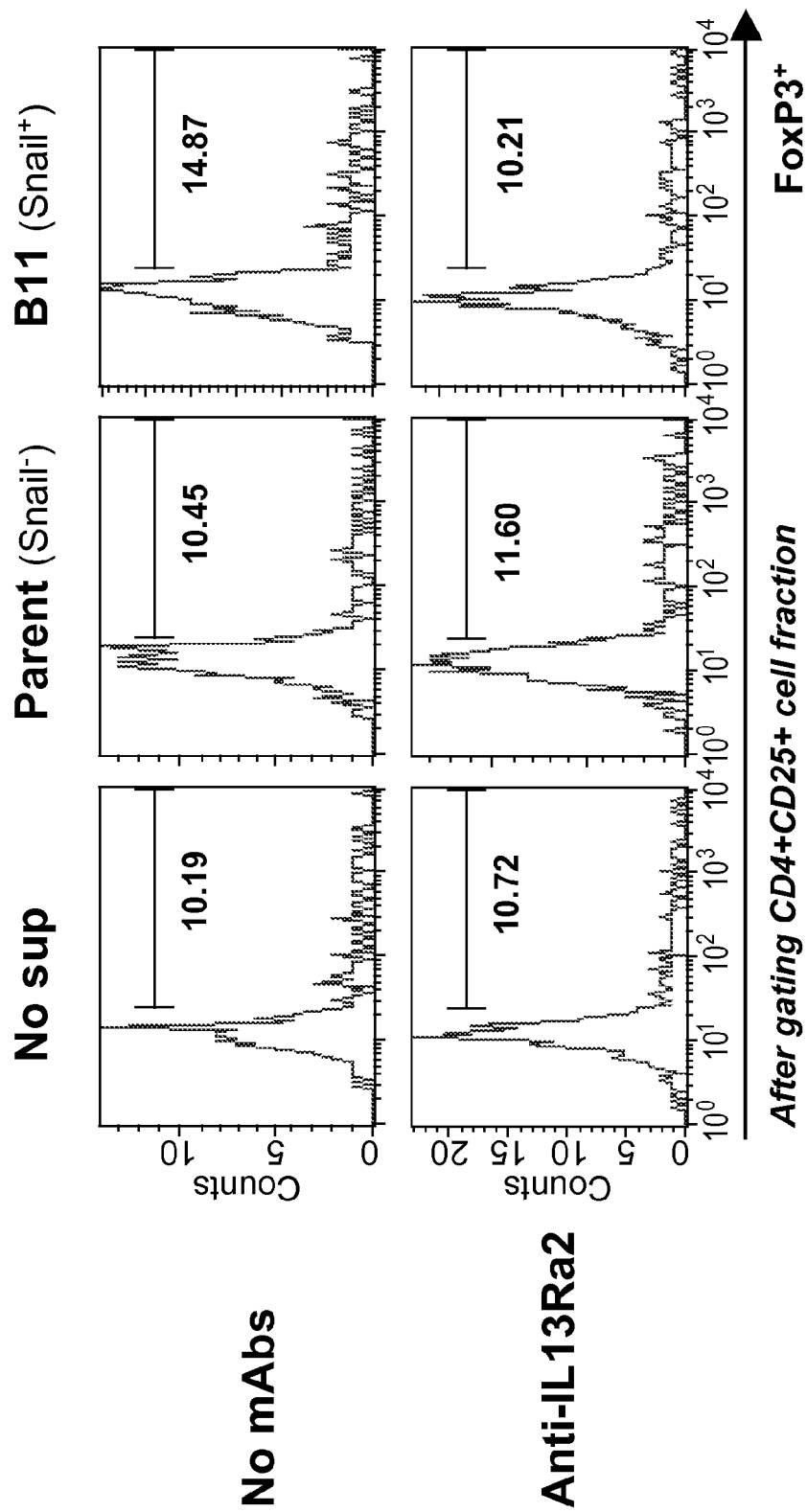
FIG. 14 shows suppression of the action of B11 cells to enhance the expression of FoxP3 protein in CD8+ cells using the anti-IL-13Ra2 antibody in one example of the present invention.

The enhancing action of the cell culture supernatant on the FoxP3 protein expression was inhibited in each of the following cases where the anti-MCP1 antibody was used (FIG. 13; 14.71 by the culture supernatant only (mIgG) vs. 11.97 by the anti-MCP1 antibody (Anti-MCP1)); the anti-TSP1 antibody was used (FIG. 13; 14.71 by culture supernatant only (mIgG) vs. 5.28 by the anti-TSP1 antibody (Anti-TSP1)); and the anti-IL-13Ra2 antibody was used (FIG. 14; 14.87 by B11 culture supernatant (No mAbs) vs. 10.21 by the anti-IL-13Ra2 antibody (Anti-IL 13Ra2)). Therefore, it is indicated that the major contributors to the enhancing action of the cell culture supernatant on the FoxP3 protein expression are at least MCP1, TSP1 and IL-13Ra2.

Thus, at least MCP1, TSP1 and IL-13Ra2 also have the enhancing action on the FoxP3 protein expression in CD8+ cells.

Figure 15:
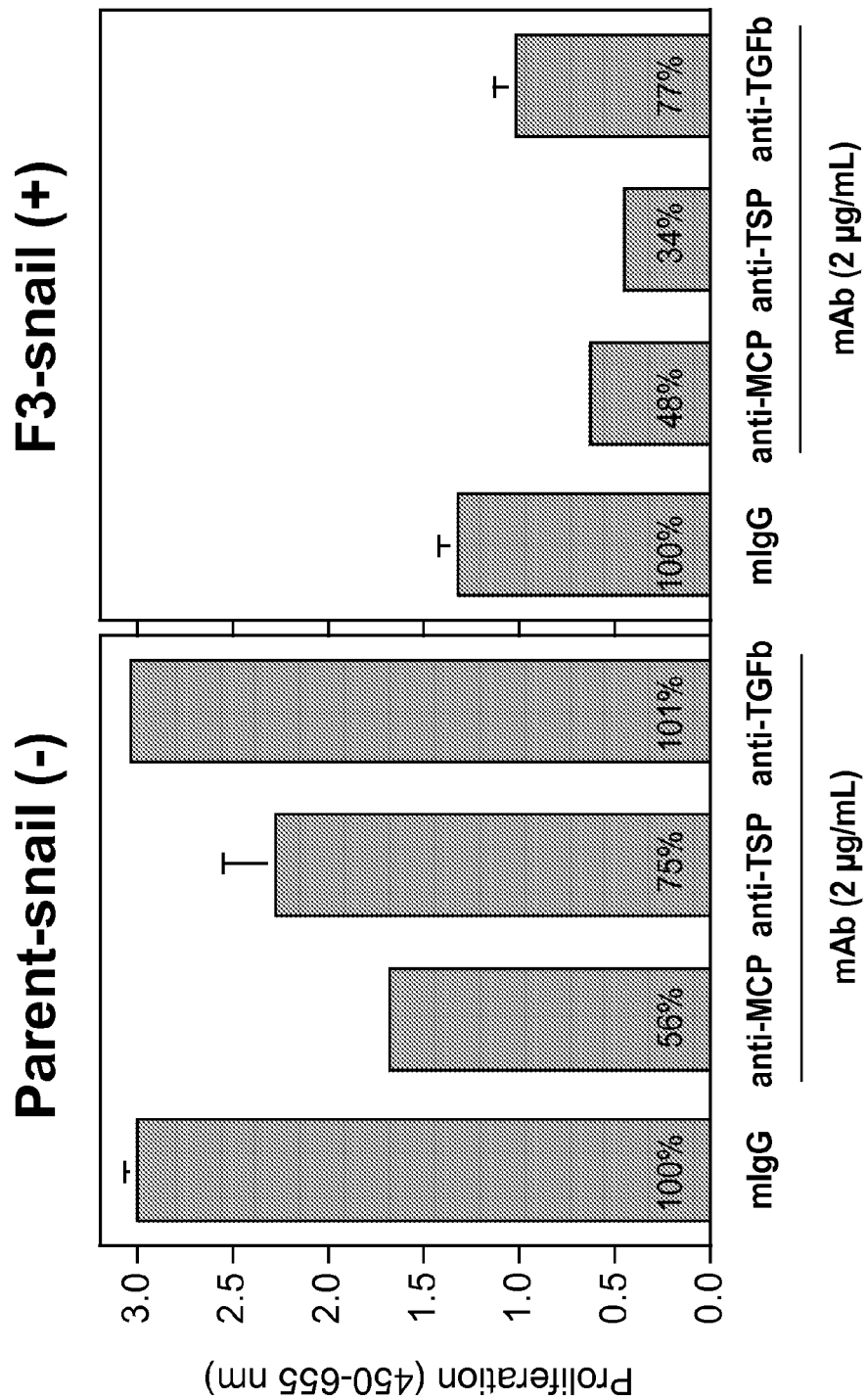
FIG. 15 shows suppression of proliferation of Snail-expressing tumor cells using the anti-MCP1 antibody or the anti-TSP1 antibody in one example of the present invention.

{14} Suppression of Proliferation of Snail-Expressing Tumor Cell Using Anti-MCP1 Antibody and Anti-TSP1 Antibody <Purpose>
It will be shown that an addition of the anti-MCP1 antibody or the anti-TSP1 antibody to the tumor cells expressing snail gene suppresses the proliferation of the tumor cells.
<Methods>
(1) Method for Measuring Cell Proliferation The anti-MCP1 antibody, the anti-TSP1 antibody or the anti-TGF-b antibody as a control was added at 2 μg/mL to the culture medium for Panc-1 cells or F3 cells, and the cells were cultured for 3 days, then for additional 4 hours after an addition of 1/10 volume of Premix WST-1 Solution (Takara Bio). Then optical density (at 450-655 nm) was measured by the microplate reader and the measured values were taken as the amounts of proliferation of the cells. Inhibition rates of the proliferation were also calculated from the measured results by bringing the value obtained with using the control mIgG to 100%.
<Results>
FIG. 15 shows the results. The anti-MCP1 antibody as well as the anti-TSP1 antibody inhibited the proliferation of both Panc-1 cells ("Parent-snail(-)" in the figure) and F3 cells ("F3-snail(+)" in the figure) by 34% to 77%. Thus, the proliferation capability of tumor cells can be reduced by inhibiting function of MCP1 or TSP1.

{15} Suppression for Infiltration of Snail-Expressing Tumor Cell Using Anti-MCP1 Antibody and Anti-FSTL1 Antibody <Purpose>

It will be shown that an addition of the anti-MCP1 antibody or the anti-FSTL1 antibody to tumor cells expressing snail gene suppresses the infiltration of the tumor cells.

<Methods>

$5 \times 10^4$ of F3 cells placed in the upper chamber of a Transwell Chamber (pore size 8 μm, BD Bioscience) with its membrane coated by matrigel were cultured overnight (37° C., 5% $CO_2$). The anti-MCP1 antibody or the anti-FSTL1 antibody was added into both the upper chamber and the lower chamber at 1 μg/mL during the culture. After complete removal of the cells above the membrane, the cells infiltrate into the lower chamber were fixed and stained using crystal violet solution, and counted under a microscope to evaluate the cellular infiltration capability. The content of the infiltrated cells were also calculated by bringing the result obtained with using the negative control (mIgG) to 100%. For the positive control, the anti-IL-10 antibody and the anti-TGF-b antibody were used.

<Results>

Figure 16:
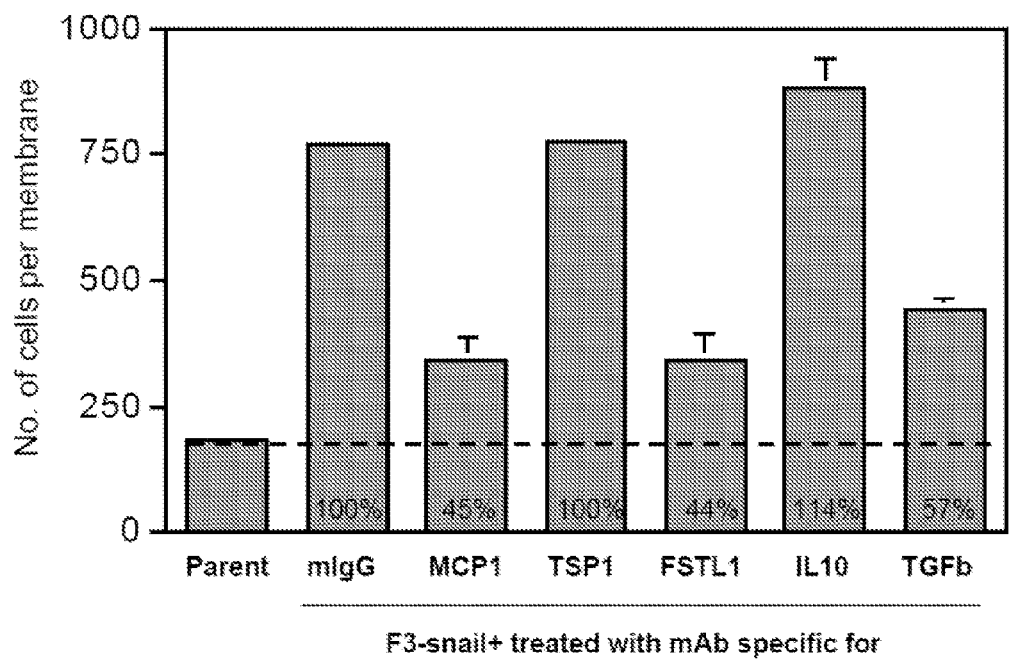
FIG. 16 shows suppression of infiltration of Snail-expressing tumor cells using the anti-MCP1 antibody or the anti-FSTL1 antibody in one example of the present invention.

FIG. 16 shows the results of the measurements for the cellular infiltration capability.

The cellular infiltration capability of F3 cells (designated as "mIgG" in the figure) was enhanced in comparison to the parent cell line of Panc-1 cells (designated as "parent" in the figure). When the anti-TSP1 antibody was added to these F3 cells, the cellular infiltration capability was not changed, whereas the cellular infiltration capability was reduced by about 45% when the anti-MCP1 antibody or the anti-FSTL1 antibody was added. Thus, the anti-MCP1 antibody and the anti-FSTL1 antibody have the action to reduce the cellular infiltration capability of Snail-expressing tumor cells.

{16} Suppression of Infiltration by Suppressing Expression of Snail in Leukemia Cell <Purpose>

It will be shown that an infiltration capability of leukemia cells can be reduced by suppressing the expression of Snail in the leukemia cells.

<Methods>

First, the expressions of Snail, MCP-1 and FSTL-1 in leukemia cell lines (Molt-3, Molt-4, UF1, KT1, K562 and MC3) were examined by RT-PCR. The same method as in {1}, {2} and {6} above was employed except that primers of the following sequences were used for MCP-1.

```
                                         (SEQ ID NO: 13)
    Forward     5'-GTGTTTGACATCTTTGAACTC-3'

(SEQ ID NO: 14)
    Reverse     5'-CCAAAGACAAACCTCACATTC-3'
```

Next, each of the leukemia cell lines (Molt-4, EL4, Daudi and KT1) in a culture medium added with the same siRNAs specific for snail gene or the control siRNAs as those used in {2}(1) above (2 μg/1×10⁶ cells/2 mL, Invitrogen) were cultured in a 6-well plate.

After 2 days of culturing, the cells were placed in the matrigel-coated Transwell Chamber (pore size 8 μm, BD bioscience) and cultured for 4 hours. Then the number of cells infiltrated through the filter was counted.

<Results>

Figure 17A:
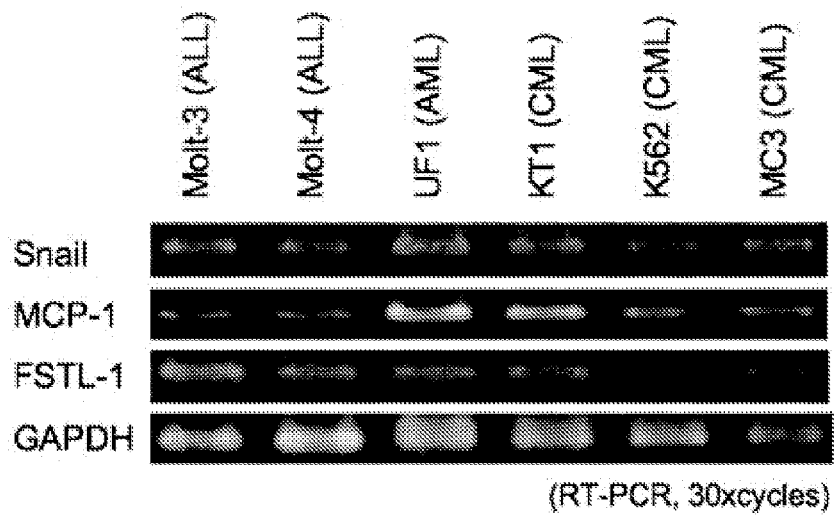
FIG. 17A shows results of analyses by RT-PCR for the expression of snail in leukemia cell lines in one example of the present invention.

As shown in the results of the RT-PCR in FIG. 17A, strong expression of Snail was detected in all the leukemia cell lines tested.

Figure 17B:
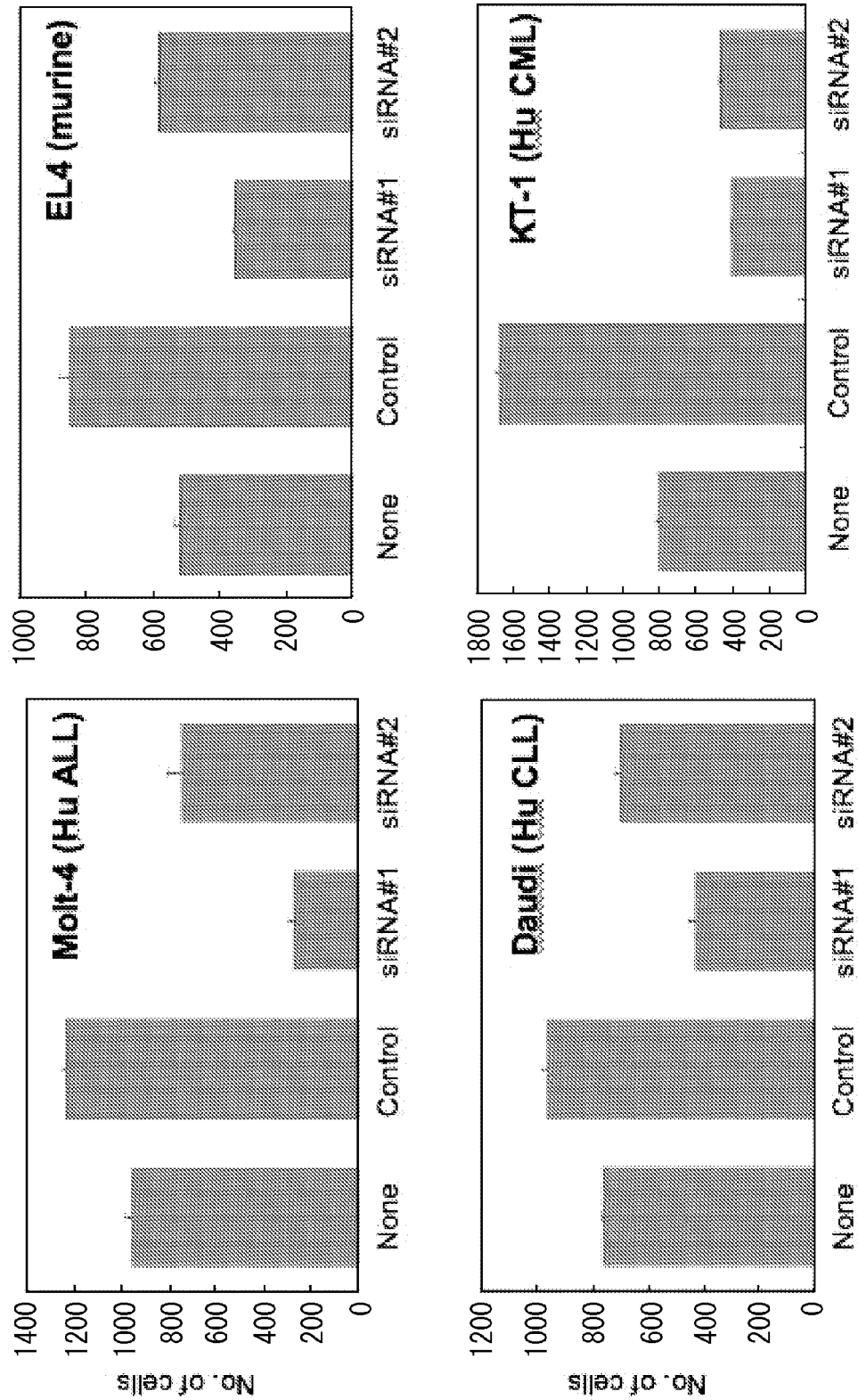
FIG. 17B shows suppression of the infiltration of leukemia cells using snail gene-specific siRNAs in one example of the present invention.

FIG. 17B shows the number of infiltrated cells counted for each of the leukemia cell lines. In all the leukemia cell lines, the infiltration capability of the leukemia cells was significantly suppressed ($P<0.001$ to $0.05$) by treating with the snail gene-specific siRNAs in comparison to the leukemia cells without the treatment with the snail gene-specific siRNAs ("None" or "Control" in the figure).

Thus, the infiltration capability of leukemia cells can be reduced by suppressing the expression of Snail in the leukemia cells. Accordingly, a substance that suppresses function of Snail is useful as an antileukemic agent.

{17} Reduction of Tumor Immunity Suppression by Tumor Cell that Inhibits the Action of Mediating Protein Produced by Snail-Expressing Tumor Cell
<Purpose>

It will be shown that a Snail-expressing tumor cell inhibits the phagocytotic action of a phagocytotic cell by which the tumor cell would be digested/eliminated via phagocytosis, and that the antibodies to MCP1 protein, IL-13Ra2 protein, IL-13 protein, IL-4 protein, CCR2 protein and IL-10 protein reduce the inhibitory action of the Snail-expressing tumor cells against the phagocytosis.

<Antibodies Used>

An anti-MCP-1 antibody: BD Pharmingen; an anti-CCR2 antibody: Abcam; the anti-IL-13 antibody: Abcam; the anti-IL-13Ra2 antibody: R&D; an anti-IL-4 antibody: BD Biosciences; and the anti-IL-10 antibody: R&D.

<Methods>

Human colon cancer cells HCT116 or the B11 clones in which snail gene had been forced to be expressed were allowed to contact with human PBMCs by coculturing for 3 days in the presence of each of the antibodies (1 μg/mL), and the PBMCs were then labeled with red fluorescence of PKH26. These PBMCs were added with the HCT116 cells labeled with green fluorescence of CSFE at a ratio of 1:1 and cultured for 2 hours at 37° C. Contents of the cells labeled with both the red and green fluorescence (i.e., the cells phagocytosing cancer cells among the PBMCs) were analyzed by the flow cytometry (FCM). In order to estimate naturally occurring phagocytosis (background), cells were cultured at low temperature (4° C.) for 2 hours.

<Results>

Figure 18:
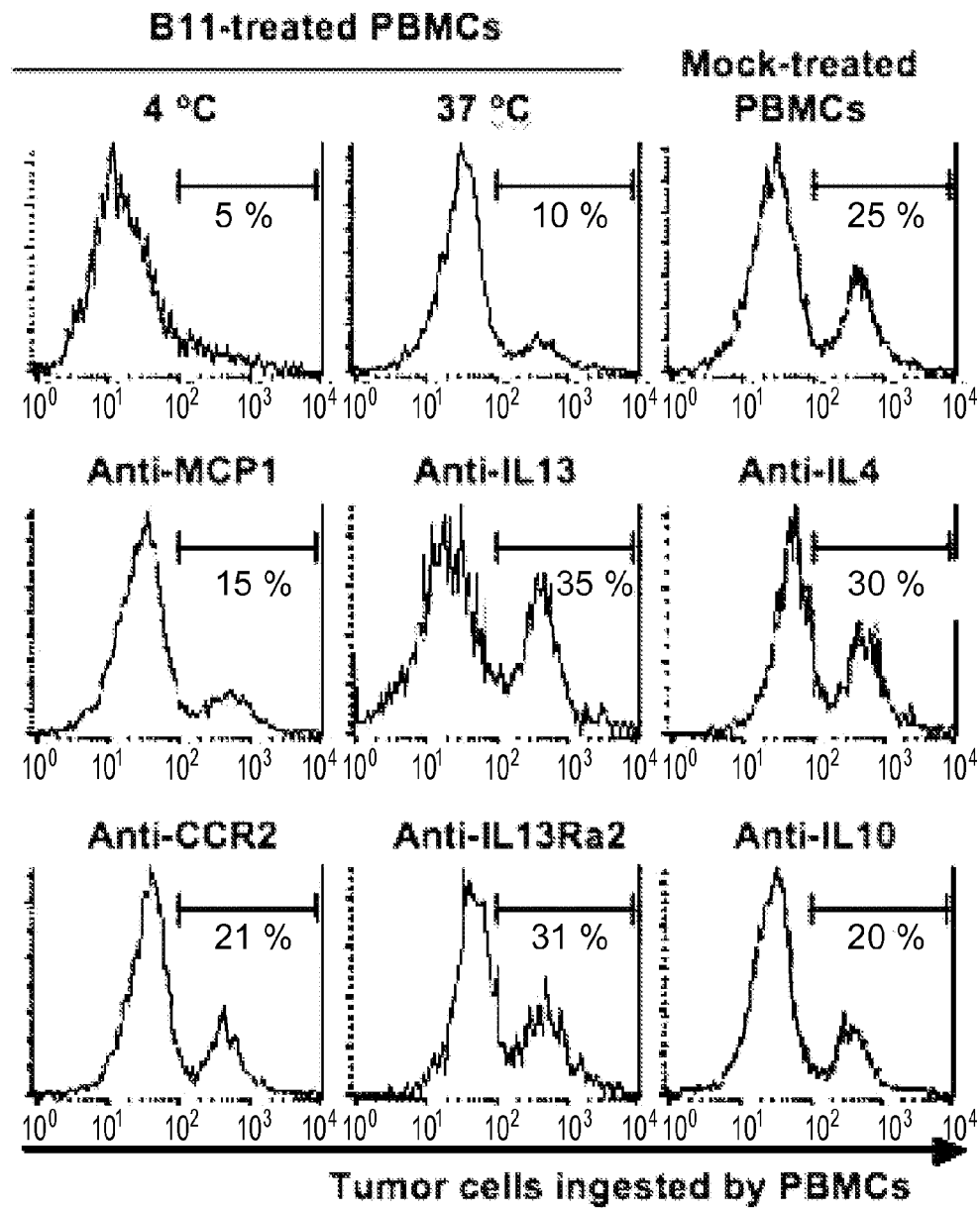
FIG. 18 shows that the anti-MCP1 antibody, the anti-IL-13Ra2 antibody, an anti-IL-13 antibody, an anti-IL-4 antibody, an anti-CCR2 antibody and an anti-IL-10 antibody reduce suppression of tumor immunity by Snail-expressing tumor cells in one example of the present invention.

About 25% of PBMCs treated with the HCT116 cells not expressing snail gene ("Mock-treated PBMCs" in FIG. 18) were labeled with both fluorescence. In contrast, only about 10% of PBMCs treated by the B11 clone ("B11-treated PBMCs" in FIG. 18) were labeled with both fluorescence. Thus, a Snail-expressing tumor cell is capable of suppressing the action of phagocytotic cells among PBMCs.

However, when each of the antibodies was added while PBMCs were allowed to contact with the B11 clone, the content of cells labeled with both fluorescence was increased to 15%~35%, i.e., the decrease of the content of the cells labeled with both fluorescence due to the contact with Snail-expressing tumor cell was prevented. Thus, by inhibiting function of the mediating protein for suppression of tumor immunity, the suppression of tumor immunity by tumor cells can be reduced, thereby stimulating the tumor immunity.

{18} Experiment of In Vivo Treatment Using siRNA Specific for Snail Gene or MCP1 Gene <Purpose>

It will be shown that suppression of tumor immunity by tumor cells can be reduced by suppressing function of Snail protein or MCP1 signaling in vivo.

<Methods>

The cells in which snail gene was forced to be expressed (H6-snail+) were generated from mouse melanoma B16-F10 in the same method as in {1} above, and transplanted to C57BL/6N mice (a subcutaneous injection with $1 \times 10^6$ cells and an intravenous injection with $2 \times 10^5$ cells were both applied to one individual simultaneously). After 7 days, the siRNAs specific for Snail or MCP1 gene or the control siRNAs (5 μg/mouse, Invitrogen) formed in lipid complexes by using PEI (Polyplus Transfection) were injected into the subcutaneously transplanted tumor.

```
The sequences of the mouse snail gene-
specific siRNAs:
                                    (SEQ ID NO: 15)
Sense         5'-GGAAGAUCUUCAACUGCAA-3'

(SEQ ID NO: 16)
Antisense     5'-UUGCAGUUGAAGAUCUUCC-3'

The sequences of the mouse MCP1 gene-
specific siRNAs:
                                    (SEQ ID NO: 17)
Sense         5'-CCAGCAAGAUGAUCCCAAU-3'

(SEQ ID NO: 18)
Antisense     5'-AUUGGGAUCAUCUUGCUGG-3'

The sequences of the control for mouse
siRNA:
                                    (SEQ ID NO: 19)
Sense         5'-CCAGAAGUACUACCGCAAU-3'

(SEQ ID NO: 20)
Antisense     5'-AUUGCGGUAGUACUUCUGG-3'
```

After 1 week, the tumor and a lung were removed from the transplanted mouse, the volume of the tumor and the number of metastatic lung nodules were measured, and intratumoral infiltrated cells were analyzed by the FACScan flow cytometer. The intratumoral infiltrated cells were collected by homogenizing the solid tumor in a culture medium, incubated with either of the antibodies to mouse antigens (anti-CD4 antibody, anti-CD8 antibody, anti-CD11c antibody and anti-1-A(b) antibody from BD Pharmingen; anti-FoxP3 antibody from eBioscience) or an H-2K(b) restrictive gp70 tetramer (peptide sequence: KSPWFTTL; from MBL, SEQ ID NO:21) at 4° C. for 1 hour, and subjected to the analysis.

<Results>

Figure 19:
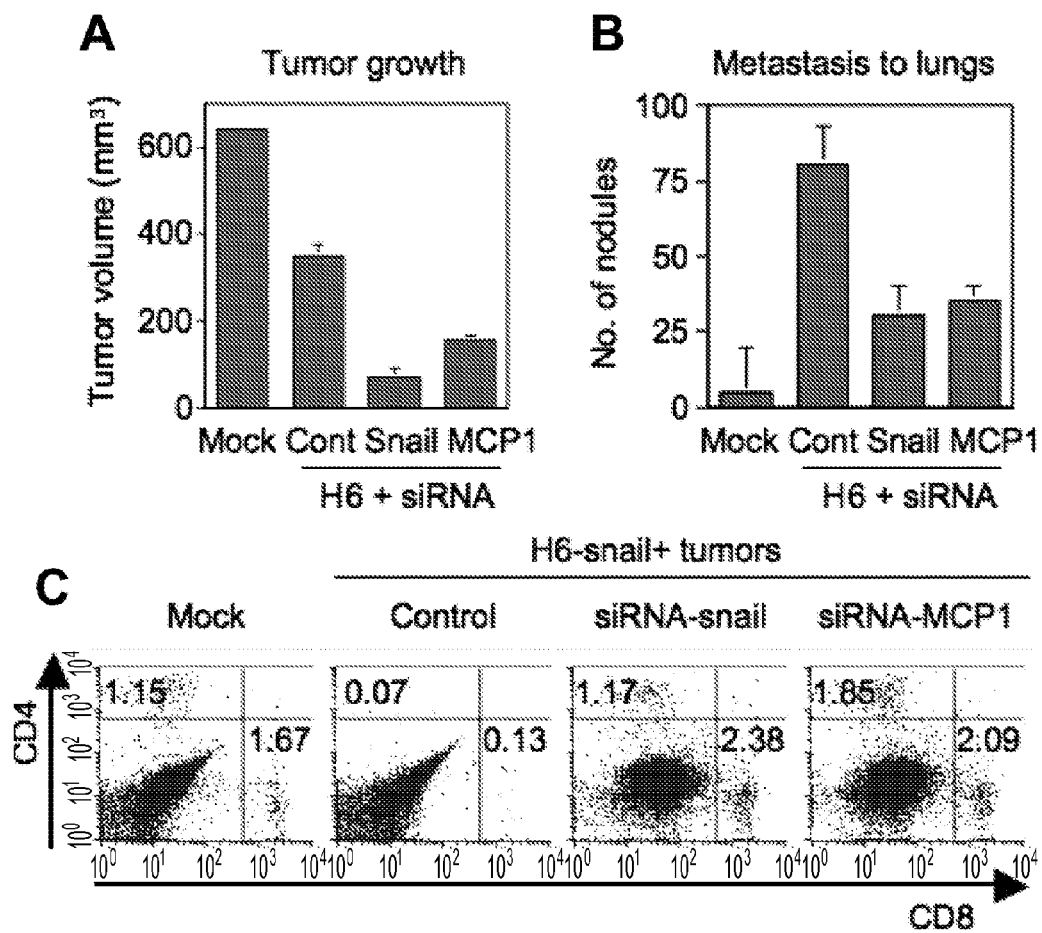
FIG. 19 shows results of an experiment of in vivo treatment using siRNAs specific for snail gene or MCP1 gene (A: measured tumor volumes, B: numbers of metastatic lung nodules, C: flow cytometry analysis for intratumoral infiltrated cells).

FIG. 19 shows the results of the measurements for the tumor volumes (A), the numbers of metastatic lung nodules (B), and the flow cytometry analysis for the intratumoral infiltrated cells (C).

As shown in FIG. 19A and FIG. 19B, in the mouse transplanted with B16-F10 ("Mock" in the figure), the growth of the tumor was significant, whereas the metastasis into the lung was little. In contrast, in the mouse transplanted with H6-snail+("Cont" in the figure), the growth of tumor was not as significant as Mock, whereas the metastasis into the lung was significantly promoted. However, when the siRNAs specific for snail gene or MCP1 gene were injected ("Snail" and "MCP1" in the figure, respectively), both the proliferation of cells and the metastasis into the lung were suppressed.

As shown in FIG. 19C, while the number of cells infiltrated into the tumor was significantly decreased in the "H6-snail+" where snail gene was forced to be expressed in comparison to the case of B16-F10 ("Mock" in the figure), the number of cells infiltrated into the tumor was increased to a level over the case of B16-F10 by injecting the siRNAs specific for snail gene or MCP1 gene.

Thus, an in vivo suppression of function of Snail protein or MCP1 signaling by using siRNAs specific for snail gene or MCP1 gene can reduce the suppression of tumor immunity by tumor cells, producing various antitumor effects such as a suppression of increase in tumor volume, a suppression of tumor metastasis, and an enhancement of infiltration of cells into the tumor.

{19} Experiment of In Vivo Treatment Using Anti-TSP1 Antibody

<Purpose>

It will be shown that the suppression of tumor immunity by tumor cells can be reduced by suppressing function of TSP1 protein in vivo.

<Methods>

$1 \times 10^6$ cells of mouse melanoma B16-F10 or H6-snail+ were transplanted subcutaneously into C57BL/6N mice, and after 7 days, an anti-TSP-1 antibody (5 μg/mouse, Calbiochem) was injected into the subcutaneously transplanted tumor, and the following assays were conducted after 1 week.

(1) The tumor volume was measured.

(2) In order to detect micrometastasis of tumor cells in various tissues (LG: lung; SP: spleen; PB: peripheral blood; BM: bone marrow), the gene expression of gp100, a cancer antigen specifically expressed by B16-F10 cells, was analyzed by RT-PCR. The same method for RT-PCR as in {1} above was employed except that the following primers were used.

```
Sequences of primers specific for gp100:
                                    (SEQ ID NO: 22)
Forward    5'-ACAGCCAGTGTATCCACAGG-3'

(SEQ ID NO: 23)
Reverse    5'-ACTTCCATTGTGTGTGTGCC-3'

Sequences of primers specific for GAPDH
as the control:
                                    (SEQ ID NO: 24)
Forward    5'-TTGACCTCAACTACATGGTCTA-3'

(SEQ ID NO: 25)
Reverse    5'-ACCAGTAGACTCCACGACATAC-3'
```

(3) Intratumoral infiltrated cells were analyzed by using the FACScan flow cytometer in the same method as in {18} above.

<Results>

Figure 20:
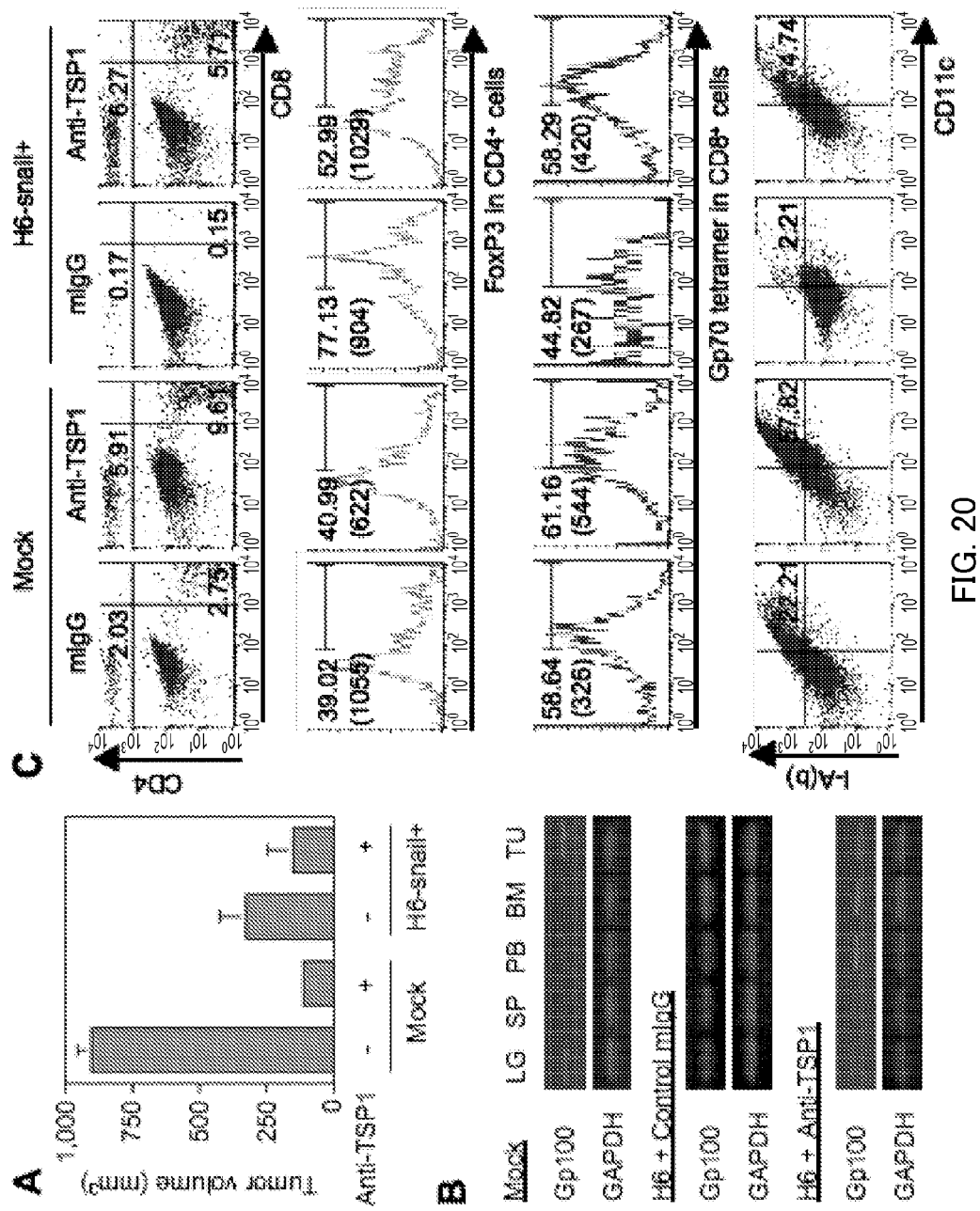
FIG. 20 shows results of an experiment of in vivo treatment using the anti-TSP1 antibody (A: measured tumor volumes, B: numbers of metastatic lung nodules, C: flow cytometry analysis for intratumoral infiltrated cells).

FIG. 20 shows the results of the measurements for the tumor volumes (A), numbers of metastatic lung nodules (B), and the flow cytometry analysis for the intratumoral infiltrated cells (C).

(1) As shown in FIG. 20A, in both cases where B16-F10 was transplanted ("Mock" in the figure) and where H6-snail+ was transplanted ("H6-snail+" in the figure), the administration of the anti-TSP-1 antibody ("Anti-TSP1+" in the figure) significantly reduced the tumor volumes.

(2) As shown in FIG. 20B, in the cases where H6-snail+ was transplanted and a mouse IgG was administered as the control of the antibody ("H6+Control mIgG" in the figure), a higher expression level of gp100 was detected in each of the tissues in comparison to the cases where B16-F10 was transplanted ("Mock" in the figure), indicating the promotion of tumor metastasis. By administering the anti-TSP-1 antibody ("H6+Anti-TSP1" in the figure), the expression level of gp100 was decreased in all the tissues, indicating that the metastasis into the tissues was significantly suppressed.

(3) As shown in FIG. 20C, while the number of cells infiltrated into the tumor was significantly decreased in the H6-snail+ where snail gene was forced to be expressed ("H6-snail+; mIgG" in the figure) in comparison to the case of B16-F10 ("Mock; mIgG" in the figure), the number of cells infiltrated into the tumor was increased to a level over the case of B16-F10 ("Mock; mIgG" in the figure) by administering the anti-TSP-1 antibody ("Anti-TSP1+" in the figure).

Thus, an inhibition of the action of TSP-1 by using an anti-TSP-1 antibody can reduce the suppression of tumor immunity by tumor cells, producing various antitumor effects such as a suppression of increase in tumor volume, a suppression of tumor metastasis, and an enhancement of infiltration of cells into the tumor.

INDUSTRIAL APPLICABILITY

The present invention can provide the followings: a gene expression enhancing method for enhancing expression of FoxP3 gene in a cell; a cell differentiation inducer for inducing differentiation of a cell into a regulatory T cell; an immunosuppressor for suppressing immunity and an agent for treating hyperimmune diseases based on the abovementioned actions; an inhibitor of enhancement of gene expression for inhibiting enhancement of expression of FoxP3 gene in a cell; an inhibitor of induction of cell differentiation for inhibiting induction of differentiation of a cell into a regulatory T cell; a reducer of immunosuppression for reducing immunosuppression, a stimulator of tumor immunity and an antitumor agent based on the abovementioned actions; and the like.

The invention claimed is:

1. A method for treating a patient with a Snail+ non-blood tumor, comprising detecting snail expression in said tumor and administering an anti-FSTL1 antibody to said patient if snail expression is detected.

* * * * *

SEQUENCE LISTING

```
<160> NUMBER OF SEQ ID NOS: 25

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
cagatgagga cagtgggaaa gg                                             22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
actcttggtg cttgtggagc ag                                             22

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
gcgagcugca ggacucuaa                                                 19

<210> SEQ ID NO 4
<211> LENGTH: 19
<212> TYPE: RNA
<213> ORGANISM: Artificial Sequence
<220> FEATURE:
<223> OTHER INFORMATION: siRNA

<400> SEQUENCE: 4
uuagaguccu gcagcucgc                                                 19

<210> SEQ ID NO 5
<211> LENGTH: 19
<212> TYPE: RNA
<213> ORGANISM: Artificial Sequence
```

```
<220> FEATURE:
<223> OTHER INFORMATION: siRNA

<400> SEQUENCE: 5
cccacucaga ugucaagaa                                                19

<210> SEQ ID NO 6
<211> LENGTH: 19
<212> TYPE: RNA
<213> ORGANISM: Artificial Sequence
<220> FEATURE:
<223> OTHER INFORMATION: siRNA

<400> SEQUENCE: 6
uucuugacau cugaguggg                                                19

<210> SEQ ID NO 7
<211> LENGTH: 19
<212> TYPE: RNA
<213> ORGANISM: Artificial Sequence
<220> FEATURE:
<223> OTHER INFORMATION: siRNA

<400> SEQUENCE: 7
gcgcgucagg acucgauaa                                                19

<210> SEQ ID NO 8
<211> LENGTH: 19
<212> TYPE: RNA
<213> ORGANISM: Artificial Sequence
<220> FEATURE:
<223> OTHER INFORMATION: siRNA

<400> SEQUENCE: 8
uuaucgaguc cugacgcgc                                                19

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
gtcaacggat ttggtcgtat t                                             21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
atcactgcca cccagaagac t                                             21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gcacaggcaa ctgtgagaaa                                               20
```

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
catagtgtcc aagggctggt          20

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gtgtttgaca tctttgaact c          21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ccaaagacaa acctcacatt c          21

<210> SEQ ID NO 15
<211> LENGTH: 19
<212> TYPE: RNA
<213> ORGANISM: Artificial Sequence
<220> FEATURE:
<223> OTHER INFORMATION: si RNA

<400> SEQUENCE: 15
ggaagaucuu caacugcaa          19

<210> SEQ ID NO 16
<211> LENGTH: 19
<212> TYPE: RNA
<213> ORGANISM: Artificial Sequence
<220> FEATURE:
<223> OTHER INFORMATION: siRNA

<400> SEQUENCE: 16
uugcaguuga agaucuucc          19

<210> SEQ ID NO 17
<211> LENGTH: 19
<212> TYPE: RNA
<213> ORGANISM: Artificial Sequence
<220> FEATURE:
<223> OTHER INFORMATION: siRNA

<400> SEQUENCE: 17
ccagcaagau gaucccaau          19

<210> SEQ ID NO 18
<211> LENGTH: 19
<212> TYPE: RNA
<213> ORGANISM: Artificial Sequence
<220> FEATURE:
<223> OTHER INFORMATION: siRNA

```
<400> SEQUENCE: 18
auugggauca ucuugcugg                                               19

<210> SEQ ID NO 19
<211> LENGTH: 19
<212> TYPE: RNA
<213> ORGANISM: Artificial Sequence
<220> FEATURE:
<223> OTHER INFORMATION: siRNA

<400> SEQUENCE: 19
ccagaaguac uaccgcaau                                               19

<210> SEQ ID NO 20
<211> LENGTH: 19
<212> TYPE: RNA
<213> ORGANISM: Artificial Sequence
<220> FEATURE:
<223> OTHER INFORMATION: siRNA

<400> SEQUENCE: 20
auugcgguag uacuucugg                                               19

<210> SEQ ID NO 21
<211> LENGTH: 8
<212> TYPE: PRT
<213> ORGANISM: Artificial Sequence
<220> FEATURE:
<223> OTHER INFORMATION: Synthetic protein

<400> SEQUENCE: 21

Lys Ser Pro Trp Phe Thr Thr Leu
1               5

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
acagccagtg tatccacagg                                              20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
acttccattg tgtgtgtgcc                                              20

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
ttgacctcaa ctacatggtc ta                                           22
```

```
<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
accagtagac tccacgacat ac                                              22
```